(12) United States Patent
Belikov et al.

(10) Patent No.: US 7,985,072 B2
(45) Date of Patent: Jul. 26, 2011

(54) METHOD AND APPARATUS FOR TOOTH REJUVENATION AND HARD TISSUE MODIFICATION

(75) Inventors: Andrei Belikov, St. Petersburg (RU); Gregory Altshuler, Lincoln, MA (US)

(73) Assignee: Rejuvedent LLC, Quincy, MA (US)

( * ) Notice: Subject to any disclaimer, the term of this patent is extended or adjusted under 35 U.S.C. 154(b) by 1097 days.

(21) Appl. No.: 10/596,535

(22) PCT Filed: Sep. 29, 2005

(86) PCT No.: PCT/US2005/034606
§ 371 (c)(1),
(2), (4) Date: Jun. 15, 2006

(87) PCT Pub. No.: WO2006/039278
PCT Pub. Date: Apr. 13, 2006

(65) Prior Publication Data
US 2007/0160958 A1     Jul. 12, 2007

Related U.S. Application Data

(60) Provisional application No. 60/702,460, filed on Jul. 25, 2005.

(51) Int. Cl.
*A61C 5/00*      (2006.01)
(52) U.S. Cl. ....................................... 433/215
(58) Field of Classification Search ............ 433/24, 433/29, 215–216; 606/10, 53–100, 246–331; 264/16–20; 427/2.26, 2.29; 424/49; 523/109, 523/120; 423/308; 607/50, 51
See application file for complete search history.

(56) References Cited

U.S. PATENT DOCUMENTS

| | | | |
|---|---|---|---|
| 4,902,498 A | 2/1990 | Agricola et al. | |
| RE33,221 E | 5/1990 | Brown et al. | |
| 5,104,319 A * | 4/1992 | Evans et al. | 433/202.1 |
| 5,194,005 A * | 3/1993 | Levy | 433/215 |
| 5,267,856 A * | 12/1993 | Wolbarsht et al. | 433/29 |

(Continued)

FOREIGN PATENT DOCUMENTS
EP     1 586 312 A1    10/2005

OTHER PUBLICATIONS

Extended European Search Report from related European Application No. 05820890.1, dated Jul. 15, 2009.

(Continued)

*Primary Examiner* — Todd E Manahan
*Assistant Examiner* — Matthew M Nelson
(74) *Attorney, Agent, or Firm* — Houston Eliseeva, LLP

(57) ABSTRACT

The present invention is a number of methods and devices for tooth rejuvenation and hard tissue modification comprising applying a layer of a peroxide-free composition to a tooth surface. The applied composition comprises an aqueous solution of one or more edible acids. The composition has a pH selected from the range of about 0.5 to 5. After the treatment the composition is removed from the tooth surface. In various embodiments of the invention the pH of the composition can range between about 0.5 and 3, a narrower range being between 1 and 1.75. Hard tissue rejuvenation comprises forming a post-treatment layer having a composition which is different from that of the hard tissue by selectively heating a porous layer on the hard tissue.

26 Claims, 15 Drawing Sheets

U.S. PATENT DOCUMENTS

| | | |
|---|---|---|
| 5,833,959 A | 11/1998 | Atsumi et al. |
| 6,247,930 B1 | 6/2001 | Chiang et al. |
| 6,309,625 B1 | 10/2001 | Jensen et al. |
| 6,726,922 B1 | 4/2004 | Peyman |
| 2001/0043908 A1 | 11/2001 | Parker |
| 2001/0044096 A1 | 11/2001 | Lindquist |
| 2002/0009693 A1 | 1/2002 | Pelerin |
| 2002/0022846 A1* | 2/2002 | Auge, II ................ 606/86 |
| 2002/0058231 A1 | 5/2002 | Friedman |
| 2002/0072030 A1 | 6/2002 | Davis |
| 2002/0106336 A1 | 8/2002 | Glandorf et al. |
| 2004/0116511 A1 | 6/2004 | Malik |

OTHER PUBLICATIONS

International Preliminary Report on Patentability, dated Apr. 3, 2007, from International Application No. PCT/US2005/034606, filed Sep. 29, 2005.

* cited by examiner

METHOD AND APPARATUS FOR TOOTH REJUVENATION AND HARD TISSUE MODIFICATION

RELATED APPLICATIONS

This application claims the benefit of U.S. Provisional Application Nos. 60/614,183, filed Sep. 29, 2004 and 60/681,630, filed May 17, 2005, both of which are incorporated herein by reference in their entirety

FIELD OF THE INVENTION

The present invention relates to the field of dental and hard tissue treatment, including but not limited to tooth surface rejuvenation and hard tissue modification.

BACKGROUND OF THE INVENTION

The health and appearance of a one's teeth is one of the main factors determining one's general health and self image, which is important for digestion, psychological, social and sexual well being. Generally, the condition of the teeth depends upon genetic, lifestyle, dietary, environmental and other factors. Human teeth are exposed to mechanical and chemical processes associated with food and beverage consumption, as well as the impact of bacteria and other natural and artificial substances and objects on a daily basis. In the modern world with its processed foods and sugary diets, teeth can be rapidly discolored, damaged, worn, eroded and even lost without daily oral hygiene and regular inspection and maintenance. Unlike other human tissues, the tooth enamel does not contain mechanisms for self-protection and rejuvenation. The enamel normally can restore itself by a remineralization process with the necessary minerals and action obtained from saliva. There is a continuous demineralization/remineralization process, which restores the health of the enamel tissue, damaged by the actions described above. The past several decades have seen the introduction of many new methods improving strength of the enamel and aiding its remineralization. Such methods include, but are not limited to, fluoridation of water, using fluoridated toothpastes containing amorphous calcium phosphate, using more effective toothbrushes, including electrical brushes, using new types of rinses, of teeth using peroxide-based agents has become increasingly popular. As a result, here has been a significant decrease in tooth loss due to caries and an improvement of teeth appearance in the countries where such methods are available.

In the United States, however, 85% of population still suffers from caries and over 30% of adults are not satisfied with the cosmetic appearance of their teeth. This situation is significantly worse in the countries with no water fluoridation. Therefore, the development of new treatment for tooth protection and rejuvenation is a very desirable objective.

Tooth Structure

Human teeth serve several functions, including chewing, aiding in speech, and the perception of beauty and facial harmony. A human tooth consists of three sequential layers of tissues: (1) the hard, highly mineralized tissue, the "enamel", supported by the less mineralized and vital connective tissue, (2) the "dentin", which is formed from and supported by soft, connective tissue, and (3) the "dental pulp" or the "pulp". The pulp consists of sensitive tissue containing blood vessels, nerve fibers, specialized cells and pulpal fluid. The dentin, which surrounds the dental pulp, forms the major part of the tooth. It is dense bonelike tissue consisting of 70% inorganic material, 20% organic material, and 10% water by weight. The enamel, which surrounds coronal dentine, consists of 96% inorganic, 1% organic material and 3% water by weight. The inorganic material is called hydroxyapatite, a substance also found in bone and dentine. A tightly packed mass of apatite crystals forms the basic structural unit of enamel, called the "enamel rod" or "enamel prism." It is shaped like a keyhole and has an average width of 5 μm. Its width is determined by the local enamel thickness, with a maximum of approximately 2.5 mm. Rods run from the dento-enamel junction perpendicularly to the outer enamel surface and are maintained in rows. Neighboring rods are separated from each other by 0.1-0.2 μm wide prism sheaths. The enamel rod consists almost entirely of hydroxyapatite, whereas the prism sheaths are made up largely of organic material comprised of amelogenin polypeptide and non-amelogenin proteins. The mineral component of enamel is an apatite like crystal, which has the formula of $Aio(BO_4)_6X_2$, where A is Ca, Cr, Ba, Cd, B is P, As, Si, and X is F, OH, $ClCO_2$. The dominant formula of enamel apatite is an ideal hydroxyapatite $Ca_{10}(PO_4)_6(OH)_2$ with the Ca/P ratio of 1.67. In addition to hydroxyapatite (~75%), carbide apatite (~3-20%), chlorine apatite (<<4%), fluorine apatite (<<0.5%) are also present in enamel. Apatite is formed in hexagonal micro crystals with a size of (14-46) nm×(27-78) nm. These crystals have the typical crystal defect in the lattice arrangement including shifted, disrupted, and curved lattice planes. Defective lattices in the boundary between crystals are fused with each other. In carious lesions, mineral dissolution begins in the crystal lattice defects. The micro crystals in enamel are surrounded by a water shell, which makes enamel transparent for some ions. The main requirements for healthy enamel are mechanical hardness, wear resistance, and caries resistance (which is essentially acid resistance). In addition, the esthetic appearance of especially the anterior teeth has become of significant importance in today's appearance conscious society.

Remineralization and Demineralization of Hard Tissue

The process of the dissolution of enamel is called demineralization. It is the result of the interaction of the enamel components with the acid, produced by the bacterial action of plaque and various foods, as well as by the consumption of acidic beverages, such as fruit juices, wine and some sports and carbonated drinks. The decrease in a pH results in the dissolution of Ca and P ions into the saliva. The solubility in acid of different types of the apatite found in the enamel varies significantly. For example, the solubility of carbonate apatite in an acid with a given pH is approximately an order of magnitude greater than that of hydroxyapatite, which, in turn, is an order of magnitude greater than that of fluorapatite.

The reverse process is called remineralization, which is facilitated by some or all of the following mechanisms. Human saliva contains calcium and phosphate in a supersaturated state, which can remineralize hydroxyapatite crystals lost during demineralization. This is the fundamental process in the prevention of enamel loss. Under normal conditions, there is a balance between demineralization and remineralization. The remineralizing ability of saliva is a typical example of the natural tooth rejuvenation mechanism. The remineralization process can also be initiated by controlling an oral fluid. The resistance of teeth to an acid attack can be increased and such methods as the use of fluoride in toothpastes and community water supplies have been known for many years. F ions from compounds, such as NaF and $SnF_2$, replace some of the OH— ions in apatite during the remineralization process. The modified enamel substance, called fluorapatite, is more resistant to acid than hydroxyapatite. Amorphous calcium phosphate ($CaPO_4$) or ACP, is another compound used to promote enamel remineralization. As the pH falls, ACP dissociates to form calcium and phosphate ions, thereby minimizing the drop in the pH and limiting demineralization. Since ACP can act as a reservoir for calcium and phosphate ions and maintain these ions in a state of supersaturation with respect to enamel, ACP decreases the process of demineralization and promotes remineralization. Remineralized complexes consisting of Ca and F have been suggested as additives to strips and filling material.

Acid Etching

Acid etching or enamel conditioning has a widespread use in clinical practice. It is most frequently used in bonding of resin materials. Different types and concentrations of acid may be used. Of these, 30-40% phosphoric acid with an application time of up to 60 seconds is the one most frequently used. Another, less frequent acid application is the removal of the superficial enamel stains resulting from the developmental disturbances of the enamel, such as excessive intake of fluoride. Reported uses involve 18% and 37% hydrochloric acid applied for up to 25 seconds.

Acid etching and partial demineralization of apatite crystals leads to the high porosity of exposed surfaces, which makes such surfaces better suited for bonding of the restorative and adhesive materials. Three distinct acid etching patterns can be distinguished. A type I pattern is the one where the enamel rod cores are preferentially removed. In the type II pattern mostly prism sheaths are removed, while the rod cores remain intact. The type III pattern is characterized by irregular and indiscriminate etching. The cause for the described differences is unclear. One explanation may be that the differences in the orientation of the c-axis of apatite micro crystals relative to the enamel surface cause the differences in the etching patterns, because the solubility of the apatite in the c-axis configuration is lower than that of the crystals in the perpendicular direction.

Acid etching of hard tissue is a cause of the enamel loss and the decrease of mechanical hardness and wear resistance. In addition, acid etching of the superficial enamel layer, which is the most resistant to acid attack, can accelerate the growth of a carious lesion. For this reason, acid is used in dentistry mainly for the treatment of hard tissues to facilitate adhesion of tooth colored restorative materials to such hard tissues. In low concentrations, an acid (pH>5) is used as an addition to peroxide bleaching agents and some rinses and toothpastes for the stabilization of various ingredients. Dentists recommend limiting the use of acidic beverages and foods. Most foods and beverages have a pH of 2.5 or more, usually between 4 and 7.

Cosmetic Appearance of Teeth

The appearance of a tooth is important in today's society. Anterior teeth play the main role in this appearance. Among the many factors, which determine the appearance of a human tooth, the most important are (a) "color", (b) "gloss", and (c) "translucency":

(a) "Color" can be described as the result of the interaction of a tooth with light, including reflection, absorption and transmission. Light in general is electromagnetic radiation, and the light visible to the human eye is characterized by the wavelength within the spectral range from about 400 nm to about 800 nm. Different wavelengths are associated with different hues, such as blue, represented by a wavelength of 470 nm, green by 540 nm, and red by 670 nm. White light contains a mixture of all of the wavelengths and is similar to sunlight. Human enamel may selectively reflect only the wavelengths from a portion of the spectrum, while absorbing and transmitting the other portions. The reflected portion determines, in part, the tooth's color. For example, a yellow enamel surface reflects mostly the yellow portion of the light spectrum and partly absorbs the blue incident wavelengths. A black surface absorbs the light of entire visible spectrum and reflects none. A white surface reflects the light of all incident wavelengths in uniform fashion. In addition to color of the surface exhibited due to reflection, a portion of the incident light may be transmitted to the dentin-pulp complex, where a portion of the transmitted light is absorbed by the blood (400-600 nm) and another portion of the incident light is reflected, affecting the tooth's color.

(b) Incident light may be reflected in a diffused or specular fashion. In specular reflection, the angle of incidence of a light beam is equal to the angle of reflection, resulting in a lustrous appearance, said to have high "gloss". This reflection takes place only from well-polished enamel surfaces with micro pores smaller than the wavelength of the incident light. In diffuse reflection, the reflected light is scattered in all directions, resulting in a decrease in gloss. High gloss is usually associated with a smooth enamel surface. In addition, a significant portion of the diffused light is reflected from the body of the enamel, the dento-enamel junction, the dentine and the pulp.

(c) "Translucency" is an optical property of an object, which allows it to transmit or scatter incident light. A highly, translucent tissue transmits most of the incident light, resulting in a more transparent and lighter colored appearance. An increase in scattering within the tissue leads to a decrease in its translucency and an increase in its opacity. Light scattering is the result of scattering at the centers within the tissue. Light scattering is affected by the size, shape, and number of scattering centers, as well as by the difference in the refractive indices between different components of the tooth.

Tooth discoloration can be classified according to the location of a stain, which may be extrinsic or intrinsic:

1. Extrinsic stains are mainly caused by the daily intake of substances, such as foods and beverages, and/or the by the use of tobacco products, etc. These substances tend to adhere to the enamel's structure and thereby discolor the teeth and/or reduce their whiteness. Most extrinsic stains are accumulated in the plaque, pellicle, tartar and the superficial enamel layer with a thickness of up to a dozen micrometers. Extrinsic discoloration typically affects the tooth enamel surface and may be classified according to its origin, and whether it is "non-metallic" or "metallic":

a) "Metallic" stains are formed as a result of exposing the enamel surface to metal salts. Such exposure can occur either via consumption of medicines containing such salts or via occupational exposure to metals, such as that found among foundry workers.

b) "Non-metallic" stains are formed on the enamel surface deposits as a result of consuming various dietary products, beverages, tobacco, mouthwashes and medicaments.

2. Over a period of years extrinsic stains may penetrate the enamel layer and gradually cause intrinsic discolorations. "Intrinsic stains" is the term used for stains, which have penetrated the tooth structure (i.e. discoloration within the tooth matrix). Intrinsic discoloration is located beneath the enamel surface and occurs as a result of changes in the physical properties or a structural composition of the tooth tissues. The exact location of a stain within the enamel has not been known with certainty. Intrinsic discoloration may be classified according to its cause, with the following types generally recognized:

(a) "Ageing" is frequently associated with thinning of the enamel and an increase in its translucency. The increase makes the dentin-pulp complex more visible, leading to an overall darkening of the teeth.
(b) "Alkaptonuria" is a condition affecting the permanent dentition, leading to brown discoloration as a result of an incomplete metabolism of tyrosine and phenylalanine.
(c) "Amelogenesis imperfecta" is a hereditary condition, where the enamel calcification is disrupted during the tooth formation, resulting in a discoloration varying from the mild "white-spot" lesions to the hard enamel with the yellow-brown appearance.
(d) "Congenital erythropoietic porphyria" is a metabolic disorder resulting from an error in the porphyrin metabolism, leading to the accumulation of porphyrins in the dentition and its red-brown discoloration.
(e) "Congenital hyperbilirubinaemia" is caused by the breakdown products of haemolysis, resulting in the yellow-green discoloration.
(f) "Dentinal dysplasias" are hereditary conditions where the primary and secondary dentition is of a normal shape and form, but may have an amber translucency.
(g) "Dentinogenesis imperfecta" is a dentine defect, which occurs genetically or through environmental influences, resulting in bluish or brown discolorations.
(h) "Enamel hypoplasia" is most likely to occur following a trauma or infection in the primary dentition. This defect is frequently accompanied by pitting or grooving, which is predisposed to extrinsic staining of the enamel, often then becoming internalized.
(i) "Fluorosis" results from an excessive intake of fluoride found in the water supply, mouthwashes, toothpastes and certain types of medication. Fluoride interacts with the enamel's hydroxyapatite crystals, resulting in brown-black stains.
(j) "Pulpal hemorrhage" is caused by a severe tooth trauma and results in a purple-pink discoloration caused by the blood pigments.
(k) "Root resorption" begins at the root surface, resulting in a pink appearance at the cemento-enamel junction.
(l) "Systematic syndromes" is represented by the defects in the enamel formation, occurring as a result of clinical syndromes, such as Vitamin D dependent rickets, epidermolysis bullosa and pseudo-hypoparathyroidism.
(m) "Tetracycline staining" is caused by systematic administration of tetracycline antibiotics during the tooth development. Tetracycline forms complexes with the calcium ions of the hydroxyapatite crystals within the dentine, resulting in a yellowish or brown-gray appearance.

An understanding of the reasons for enamel discoloration is helpful for the in-depth understanding of the proposed method and device for tooth whitening. A child's or adolescent's teeth are much whiter than those of an adult, as with age, teeth discolor. This discoloration is caused by the consumption of foods and beverages containing natural dyes, smoking and other external causes. An additional cause, independent of these, is the structure of the tooth enamel, which is affected by aging. At a younger age teeth are whiter, because enamel has a high porosity and its prisms are randomly oriented. A material with such a structure scatters light very well. The better the scattering properties of the enamel, the whiter its appearance. Over its lifetime, the enamel hardens, the size of the prisms increases and their orientation relative to each other becomes more orderly. These changes cause the enamel to gradually loose its scattering properties and become more transparent, allowing light to penetrate to the underlying dentin, and be scattered and reflected, resulting in the observer's seeing a color influenced by the color of the dentin, which is more yellow. For humans this process occurs from about the age of 40. Ignoring external factors (oral hygiene, coffee, tea, wine and tobacco consumption, and trauma, etc), the objective of tooth whitening relates to whitening enamel and reconstructing its scattering properties, mostly in the superficial layer. Existing whitening methods, such as those utilizing hydrogen peroxide, do not address this problem effectively because they mostly bleach the superficial stains.

Tooth Rejuvenation

Tooth rejuvenation is one of the most important parts of preventive and esthetic dentistry. As explained above, it can be a part of the natural process, facilitated by the saliva. However, in many cases the natural role of the saliva may not be enough to keep a tooth from degradation. Several methods aimed to enhance tooth rejuvenation exist. Most are focused on the improvement of one the components of tooth rejuvenation, and do not provide a complete solution. Such methods are: water fluoridation, mouth rinses, gels and strips, tooth brushing, professional oral cleaning, tooth whitening, tooth coating, tooth surface laser modification. These methods are described below in more detail.

1. Water fluoridation contributes to the formation of fluorapatite in the external layer of the enamel. Fluoride in water plays several roles in the prevention of dental caries, such as the inhibition of acid production in plaque, the enhancement of remineralization of carious lesions and strengthening the enamel against an acid attack through the formation of the fluorapatite ($Ca_{10}(PO_4)6F_2$) this effect takes place at low concentrations of fluoride. High concentrations of fluoride can cause the formation Of $CaF_2$ and the destruction of tooth structure.

2. Mouth rinses are mainly used for bacterial reduction. Some additives, such as the casein phosphopeptide-amorphous calcium phosphate nano-complexes, have been proven to be effective in the remineralization process.

3. Different types of gels and strips and have been shown to provide an antibacterial effect. A gel, containing fluoride, calcium and phosphate ions, has been shown to be effective in the remineralization process. Preliminary treatment of enamel with low acid concentrations enhances the effect of the fluoride treatment. Gels or strips may also include peroxide for tooth whitening.

4. Tooth brushing and flossing are the most important forms of preventing tooth stains and destruction of teeth, since they are daily regimens. The mechanical cleaning of the teeth removes a biofilm, prevents/decreases the build up of tartar and decreases acid production by bacteria. It also enhances the access of saliva to the enamel, in the process improving the chances for remineralization. In addition, toothpastes often contain antibacterial, remineralizing and whitening components.

5. Professional oral cleaning in the dental office provides additional benefits to the methods of tooth brushing and flossing, such as the removal of supra and subgingival plaque and calculus, plaque detection, and application of caries-preventing agents. The treatment typically involves the procedures, such as scaling and polishing of teeth and subgingival curettage, resulting in a more effective method of preventing of periodontal or other dental diseases, as well as an overall aesthetic improvement in the appearance of teeth and gums. Plaque detection and the application of the caries-preventing agents may also be performed by the health professional as an aid to home care and remineralization. However, this treatment is not capable of removing intrinsic and deep extrinsic stains.

6. Tooth whitening has been one of the fastest growing tooth rejuvenation procedures during the last decade. Prior to tooth whitening, a correct diagnosis of the cause of the discoloration needs to be made. Certain extrinsic stains, which occur on the surface or subsurface of the teeth, can be removed by mechanical means. Not all extrinsic stains can be removed mechanically. Some stains are better removed with the whitening agents, which inhibit non-enzymatic browning reactions. Intrinsic stains are located in the tooth matrix and cannot be removed by intense mechanical brushing of the teeth. Removal of intrinsic stains calls for the whitening agents capable of penetrating into the tooth structure. Three types of whitening treatments are available: a) "mechanical abrasion", b) "acid abrasion", and c) "peroxide bleaching".

a) Mechanical abrasion is used for the removal of superficial extrinsic stains, mostly accumulated in tooth plaque, pellicle and tartar. Extrinsic stain removal is is achieved manually and mechanically by machine scaling followed by mechanical brushing with abrasive cleansing agents. The brushing step is performed with either a regular toothbrush or rotary instrumentation. The cleansing agents usually contain abrasives and surfactants, typically found in modern toothpastes, or dental pumice.

b) "Acid/abrasion" whitening involves the removal of a stained tooth structure and tooth stains simultaneously to a depth of approximately 100 μm. The first published tooth whitening technique, reported by Chaple in 1877, used oxalic acid. Modern techniques involve etching of the enamel surface by an 18% hydrochloric acid solution, followed by mechanical abrasion. This technique has been suggested for the removal of brown stains associated with an excessive fluoride intake. This technique is destructive and time consuming, so the concerns are raised about the safety of the soft tissue and damage to it due to the low pH of the acid used. Another drawback of this technique is the lack of predictability of the results, because it is typically difficult for a clinician to ascertain the probable depth of the stain, which significantly limits the use of the technique in everyday practice.

c) The first report of "peroxide bleaching" was published by Harlan in 1884. Although many whitening agents have subsequently been suggested, peroxides remain the most commonly used teeth bleaching compounds. Peroxide bleaching works by oxidation—the chemical process in which hydrogen peroxide ($H_2O_2$) releases free radicals ($HO_2+O_2$), with unpaired electrons, which are given up to the bleached substance, oxidizing it and making it lighter in color. In dental bleaching, hydrogen peroxide diffuses through the organic matrix of the enamel and oxidizes the organic material located in the prism sheaths. Peroxide whitening techniques are usually divided into two main categories: "non-vital" and "vital":

The non-vital techniques (treatment of a tooth with a non-vital or endodontically treated pulp) often provide very good results, but they have limitations and potential hazards. These limitations and hazards include a potential root resorption if the bleaching agent is placed below the coronal portion of the tooth. One non-vital whitening technique uses sodium perborate and 35% hydrogen peroxide as the active ingredient.

Products sold for vital whitening techniques can be divided into three main groups: (i) "in-office" whitening products, (ii) dentist prescribed, home-applied whitening products, and (iii) over-the-counter whitening kits and toothpastes.

i. One of the most commonly used "in-office" techniques combines the use of 35% hydrogen peroxide with heat and light treatment to speed up the oxidation reaction (i.e. the removal of stains), ii. Another method, using a "dentist prescribed, home-applied" whitening product, involves the use of 10% urea peroxide (carbamide peroxide). An individually fabricated mouth tray is constructed for a patient, the whitening agent is placed into this tray which is then worn by the patient for an appropriate period of time.

iii. Whitening kits can be used for whitening teeth and include products, such as toothpastes and mouthwashes having from 3% to 6% hydrogen peroxide. Such whitening kits are sold directly to consumers without a prescription from a dentist.

Generally, there are three variables that can be varied to control the rate of whitening during the procedure utilizing the peroxide agents. The first variable is a concentration of the peroxide. In order to make the procedure occur within a reasonable period of time, concentrations of peroxide equivalent as high as 35 percent by weight are used. The peroxide-based whitening composition can be in a liquid, paste or gel form, with the gel being the most popular. The second variable is the exposure time, i.e., the time during which the tooth is exposed to the peroxide. The third variable is a pH of the peroxide mixture.

Peroxide tooth whiteners with a higher pH are more effective than the identical ones with a lower pH. Unfortunately, a higher pH also means the decreased peroxide stability. Consequently, none of the present tooth whitening materials have a pH much above neutral, while most are actually acidic. The only exceptions are those materials requiring an addition of an alkalinity adjuster immediately prior to use, but this approach has little consumer or professional appeal because of the complex handling and preparation procedures involved.

Another problem in designing a desirable tooth whitening product is a lack of a good gelling material which can be used at the higher pH ranges. Virtually all of the current stable tooth-whitening gels use a carbomer matrix. Carbomer in its initial gelled form has a low pH. An increase in pH leads to a loss of viscosity and stability of the carbomer, requiring great skill and effort to keep the material useful above a neutral pH. As a result, the only single-tube, high-concentration peroxide gel product to ever reach the marketplace (Ultradent of Salt Lake City, Utah) is so sensitive to destabilization by heat exposure that the manufacturer refuses to ship during certain weather conditions or over a weekend. Once received by a dentist, the material needs to be refrigerated at all times, or its efficacy is at risk. An end user is left with a product, which has unpredictable and unsatisfactory characteristics, since its effectiveness can be completely destroyed by a common uncontrollable event, such as a slow shipment.

Thus, the efficiency of whitening teeth, the safety of the procedure and the stability and shelf life of whitening agents present significant obstacles to their successful use. A further problem is that effective concentrations of hydrogen peroxide exceed the concentration limits allowed in certain countries. Products comprising a low concentration of whitening agents, such as hydrogen peroxide, are considered to have a slow whitening effect. Therefore, there is a need for providing safe tooth whitening compositions, which do not contain harmful concentrations of peroxide. It is further desirable that such tooth whitening materials be used as the components in conventional oral care products for "home-use". To date, tooth whitening has been accomplished by using peroxide as the bleaching agent. When peroxides decompose, they release oxygen, which denatures the proteins, which act as pigments. The main problem in using them is that the required high concentrations of peroxide are less safe when those used intraorally. A further problem is that the peroxides are unstable and have a short shelf life.

7. Coating the external surface of the tooth or other hard tissues is one of the most effective methods of changing its appearance and protecting it from an acid attack. Several light cured compounds for the protection of the enamel surface, such as BISCOVER™, have been proposed. Such methods are either very destructive (veneers), or discolor and wear rapidly, thereby losing their effect (polymer-based coating materials and flowable resin composites).

8. Teeth function in an environment of mechanical, chemical and thermal stress. With normal chewing, a modest stress of 20 MPa is applied to the tooth more than 1000 times a day. Occasional stress can be up to 100 MPa. This cyclic loading occurs in a water-based fluid environment that can have a pH from 0.5 to 8 and the temperature variations of 50° C. Many different restorative materials have been developed, designed to retain their strength and properties in an aggressive environment (for example, ceramic-based porous alumina infiltrated with lanthanum aluminosilicate glass, or porous zirconia later infiltrated with glass). Porcelain, the most popular material, has excellent color properties, but is brittle and relatively easily fractured unless it is reinforced or strengthened. Porcelain restoration treatment also destroys the tooth structure, since it usually requires tooth preparation and is expensive and time consuming. These restorative materials are used for crowns or veneers and, if done properly, provide excellent esthetic appearance and prevent caries. However, the risk of recurrent caries still exists. Since any destruction of the tooth substance is harmful, clinicians have been attempting to develop non-destructive, or minimally destructive methods for tooth restoration. One such area of research involves the use of lasers.

Tooth or other hard tissues' surface laser modification is a method of selectively heating the superficial layer of hard tissue to high temperatures below or above the melting temperature of its mineral components. After cooling, a layer of newly modified material is created on the tooth surface. This layer can be more resistant to an acid attack, have a lower porosity, higher hardness and wear resistance than the original enamel or dentine. Such selective heating can be achieved in the oral cavity using a laser. The first laser modification of enamel with increased acid resistance was demonstrated in 1964. Subsequently, other lasers have been studied: the UV excimer laser (ArF laser: 0.193 µm, the KrF: 248,308 µm), the solid-state laser (Ruby: 0.69 µm, the Nd:YAG 1.06 µm, the Ho:YAG 2.06 µm, the Er:YAG 2.9 µm) and gas lasers ($CO_2$: 9.6 µm, 10.6 µm). Heating of the enamel up to a temperature of 400-600° C. leads to a significant loss of carbonate and an increase in the enamel's acid resistance. Further heating to the melting temperature (800-1400° C.) of the mineral components of the enamel, but below ablation thresholds, induces a recrystallization process forming a new structure of the superficial layer with better mechanical and acid resistance properties. This effect was demonstrated for the sealing of early pit fissure caries. A 5 min fluoride treatment in carious-like enamel (1.23% acidulated phosphate fluoride gel, pH=4), followed by a laser treatment with a $CO_2$ laser (9.6 µm wavelength, 1 J/cm2 fluence, 2 µs pulsewidth) dramatically increases the fluoride content in 1 µm of the superficial layer of enamel and significantly increases its acid resistance. Successful tooth surface laser modification requires precise adjustment of laser parameters. Most studies of the tooth surface laser modification show such side effects as carbonization, tooth darkening, crack formation in the modified enamel layer, and/or instability to thermocycling. In addition, the risk of overheating the tooth pulp exists. Finally, tooth surface laser modification has not been used in daily dental practice and no such product is currently available on the market.

SUMMARY OF THE INVENTION

The goal of the present invention is the development of a new method and apparatus for tooth rejuvenation and tooth protection and to provide a solution for the improvement of the mechanical and chemical resistance of tooth substance and to improve its esthetic appearance. Tooth rejuvenation is defined as the changing of the tooth structure leading to an increase in some or all of the following parameters: wear resistance (mechanical resistance), resistance to chemical and/or bacterial attack, and the restoration and improvement of tooth appearance and other tooth improvements.

One of the embodiments of the present invention is a method for tooth rejuvenation comprising applying a layer of a peroxide-free composition to a tooth. The applied composition comprises an aqueous solution of one or more edible acids. The composition has a pH selected from the range of about 0.5 to 5. After the treatment the composition is removed from the tooth. In various embodiments of the invention the pH of the composition can range between about 0.5 and 3, a narrower range being between 1 and 1.75.

Another embodiment of the method of the present invention comprises applying to a tooth a layer of a tooth rejuvenating composition. The composition comprises an aqueous solution of one or more edible acids. The composition also comprises ions of the elements selected from the following group: Ca, Cr, Ba, Cd, Mg, P, As, Si, F and combinations thereof. The composition has a pH selected from the range of about 0.5 to 5. At the end of the treatment the rejuvenating composition is removed from the tooth. As in the previous embodiment, the composition is characterized by a pH ranging from about 0.5 to about 5. The preferred pH interval could range between about 0.5 to about 2.5.

Yet another embodiment of the invention is a method for tooth rejuvenation in which a layer of composition is applied to a tooth. The composition comprises an aqueous solution of one or more edible acids, and is characterized by a pH selected from the range of about 0.5 to 5. The next step is heating the composition to a temperature no higher than 60° C. After the treatment is over, the composition is removed from the tooth. The heating of the composition can be performed by acting on the composition with pulsed heating source, which, for example, could be a pulsed laser source with a shorter than 1 second width and a lower that 0.4 duty cycle.

In the above-described embodiments the preferred acids are carboxylic acids, although it is contemplated that other edible acids can be used. All of the described methods can further comprise a step of applying a remineralization compound to the tooth surface. The steps of applying the rejuvenating composition and the remineralization compound can alternate up to 20 or more times, depending on a particular application and the setting in which the described methods are practiced.

Furthermore, the present invention is a tooth rejuvenating composition comprising an aqueous solution of one or more edible acids having a pH within the range from about 0.5 to about 3, and not containing peroxide. The rejuvenating composition can also comprise Ca, Cr, Ba, Cd, Mg, P, As, Si, F as a chelating agent.

Furthermore, the present invention also is a tooth rejuvenating article of manufacture with a porous material and an aqueous solution of one or more edible acids and no peroxide.

The edible acids are characterized by a pH from within the range from about 0.5 to about 5. One of the embodiments of the invention is also a capsule comprising a composition with an aqueous solution of one or more edible acids having a pH from within a range from about 0.5 to about 5 with no peroxide.

Also, the present invention is an applicator for rejuvenating treatment comprising a housing with a capsule. The capsule comprises a composition with an aqueous solution of one or more edible acids having a pH from within a range from about 0.5 to about 5 and no peroxide. The applicator also has a delivery system coupled to the capsule, which delivery system is a brush or a porous material or an injector.

It is a further embodiment of the invention, which is an apparatus for rejuvenating hard tissue. The apparatus has a housing with a capsule comprising an aqueous edible acid composition. The apparatus also has a heating element for heating the acid composition, a temperature sensor for monitoring the temperature of the acid composition, a control system connected to the heating element and the temperature sensor. The temperature sensor serves to maintain the temperature of the acid rejuvenation composition at a desired temperature, the control system serves to activate an indicator when the desired temperature is achieved. The apparatus also has a power supply for providing power to the heating element upon activating a switch, and an applicator for applying the acid composition onto external surface of hard tissue.

Another embodiment of the present invention is an apparatus for rejuvenating teeth, comprising a light source for illuminating and heating teeth, which source is connected to a control power block and serves to generate light in a range of wavelengths. The range of wavelengths is selected such that a coefficient of absorption of a composition comprising an aqueous solution of one or more edible acids and having a pH from within a range from about 0.5 to about 5 is higher than that of a tissue surrounding teeth. The apparatus also comprises a detachable mouthpiece coupled to the light source.

And another embodiment of the invention is an apparatus comprising a first portion spaced apart from a second portion. The two portions are disposed in the hand-held apparatus. The first portion serves to contain an acid-based tooth rejuvenation composition, the second portion serves to contain a second composition when the apparatus is in operation. The embodiment also comprises a chamber connected to the first and the second portions, and a mechanism for propelling the acid-based tooth rejuvenation composition and the second composition into the chamber.

Also and embodiment of the invention is a method of tooth rejuvenation comprising impregnating a porous layer of the tooth with particles, impregnating the porous layer with a compound capable of polymerizing when exposed to light, and exposing the compound to light to induce polymerization.

A further embodiment of the present invention is an apparatus for selective heating of a tooth surface with a main unit comprising one or more sources of heating energy, a cooling unit and a control unit. The apparatus further comprises a hand piece flexibly coupled to the main unit by a flexible connection, The hand piece comprises a tip serving to transmit the heating energy capable of heating a surface layer of a hard tissue between 700° C. and 2000° C.

An inventive method of tooth rejuvenation is accomplished by selectively heating a porous layer of the tooth to cause the porous layer to fuse.

An inventive method of tooth rejuvenation is accomplished by impregnating a porous layer of the tooth with particles. The particles are such that their a fluidity temperature is lower than a melting temperature of a hard tissue of the porous layer. Further, the method is accomplished by selectively heating the porous layer to a temperature lower than that the melting temperature of the hard tissue, but higher than the fluidity temperature of the particles, therefore liquefying the material of the particles. Furthermore, then the particles are let to solidify.

An inventive method of tooth rejuvenation is accomplished by impregnating a porous layer of the tooth with particles. The particles are such that their fluidity temperature is about the same as a melting temperature of a hard tissue of the porous layer. The method then comprises selectively heating the porous layer to a temperature higher than the melting temperature of the hard tissue, causing the hard tissue and the particles to fuse.

An inventive method of tooth rejuvenation is practiced by impregnating the porous layer of tooth with particles having a fluidity temperature higher than a melting temperature of a hard tissue of the porous layer. Then the method comprises selectively heating the porous layer to a temperature higher than the melting temperature of the hard tissues, but lower than the liquidation temperature of the particles.

An inventive method of hard tissue rejuvenation is practiced by filling the porous layer of the hard tissue with a fluidified material preheated above at least its fluidity temperature and letting the fluidified material cool and solidify in the porous layer.

An inventive method of rejuvenation is practiced by impregnating a porous surface with particles. The particles are such that their a fluidity temperature is higher than a melting temperature of a hard tissue of the porous surface. Then the method comprises filling the porous surface with a material preheated above its fluidity temperature, wherein the fluidity temperature of the material is lower than a melting temperature of the particles and that of the hard tissue.

An inventive method of tooth rejuvenation comprising forming a post-treatment layer having a composition differing from that of the hard tissue of the hard tissue by selectively heating a porous layer on the hard tissue.

An inventive method for tooth rejuvenation is practiced by applying to a tooth a layer of a composition comprising an aqueous solution of one or more edible acids. The composition has a pH selected from the range of about 0.5 to 5 and contains up to 10% of peroxide. The method further comprises removing the composition from the tooth.

BRIEF DESCRIPTION OF THE DRAWING FIGURES

FIG. 7 is a schematic illustration of another embodiment of a home-use device for.

DETAILED DESCRIPTION OF THE INVENTION

Figure 1:
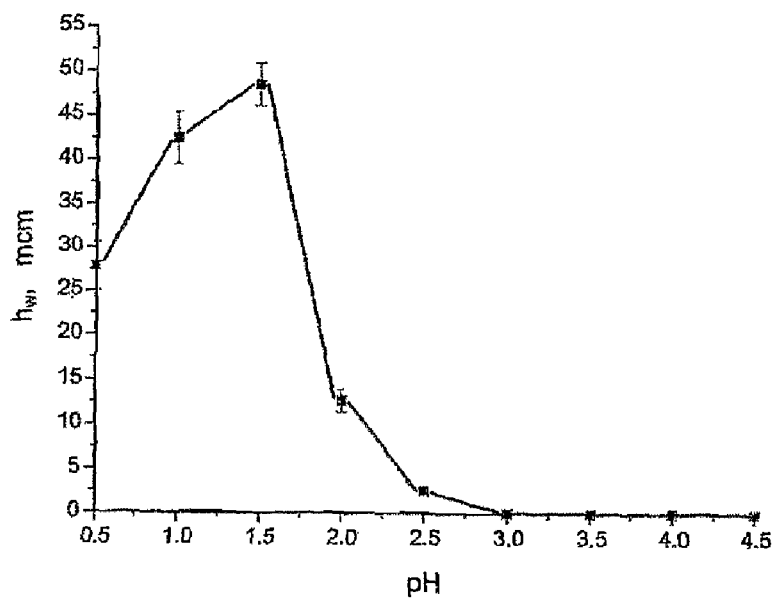
FIG. 1 is a graph showing an etched tooth enamel depth as a function of the pH of an aqueous solution of citric acid at temperature T=50° C. and exposure time t=10 min.

The present invention discloses a new method and apparatus for tooth rejuvenation and a protection, based upon the use of a high-concentration (low pH) of one or more acids, with simultaneously controlled heating and subsequent post-acid chemical or selective heat treatment. Tooth rejuvenation is defined as such a change in the tooth structure that leads to enhancement of some or all of the following parameters: mechanical hardness, chemical and/or bacterial resistance, and/or restoration and/or improvement of its cosmetic appearance, such as whitening, color alternation and other improvements of a tooth. The present invention is based on a new finding that acting with a high concentration of an edible acid on the hard and soft dental tissues, followed by selective heating leads to the previously unknown tooth rejuvenation results, The Impact of Edible Acid-Based Compound on Enamel, Dentine and Gingival Tissue The present invention uses an aqueous solution of one or more edible organic acids, including, but not limited to, acetic acid, citric acid, tartaric acid, lactic acid, fumaric acid, malic acid, maleic acid, ascorbic acid, adipic acid, sorbic acid, and others. Benzoic acids and inorganic phosphoric acids can also be used in the whitening materials as described herein. These acids are used at a high concentration and a low pH, ranging from about 0.5 to about 5. When an aqueous solution of one or more of these acids reacts with a tooth surface, the acids etch a thin layer of the enamel of approximately 0.5 to 100 microns. This etching creates a surface with much better light reflection properties, leading to a whiter appearance of the tooth. In addition, some etched enamel is better suitable for remineralization and thermal modification than non-etched enamel. Edible acids are safe for consumption and do not irritate the mouth. They are normally consumed in the foods, such as soda and fruit, so typically no permission of a regulatory authority is needed to use such acids for cosmetic applications. These acids are often used as preservatives and flavor additives in the food industry, for example, in baked goods and alcohol-free beverages, concentrates, jams, sauces, etc. Carboxylic acids, which are organic compounds with one or more carboxylic acid groups, are the preferred acids for with the whitening compositions of the present invention.

The inventors conducted a series of tests to determine the optimal pH, temperature and time for tooth rejuvenation, and for designing various devices for the tooth rejuvenation procedure. The goal of the optimization is to minimize the time of effective treatment and to maintain the safety of the surrounding tissue. The inventors suggest, without limiting themselves to any particular theory or explanation, that the following rejuvenation process occurs on a tooth surface during etching of the surface with an acid-based composition. The enamel surface is not homogeneous, it contains inorganic components, such as hydroxyapatite, in the form of crystals oriented towards its surface. The enamel surface also contains organic components, such as proteins. When the organic and inorganic components are exposed to an aqueous acid solution, such exposure leads to the deconstruction and removal of these components to a certain depth into the enamel, forming a superficial porous layer. Stains, bacteria and the weak components of the enamel are removed from the porous layer, bleached or destroyed by the acid. Exposure time, pH and the concentration and temperature of the solution all affect the depth of tissue treatment and structure of surface after treatment. The removal and bleaching of the organic component is important because this component contains the most pigment. The organic component is however, tightly bound to the inorganic component, which occurs during tooth formation and is not affected by factors such as frequency of tooth brushing, or the type of toothpaste used. Because of this, bleaching removes both the organic and the bonded inorganic components.

A test on teeth with pigmented enamel showed significant change in color, with an etching depth of several to tens of microns. The ability of an aqueous acidic solution to deconstruct and dissolve both organic and inorganic components depends on the period of time, pH, concentration, and temperature at which the process occurs. The color of the enamel after stain removal and bleaching is determined by how closely the structure after etching matches the natural structure and how well light is scattered from the surface of the tooth. Remineralization is however, a slow process, so caution in carrying out the procedure is recommended, and it is desirable to protect the new surface with a hard material. To achieve this, the present invention proposes the use of a high concentration of acid to minimize the time of treatment. For a high concentration of acid to be used safely within the oral cavity, two fundamental safety concerns need to be addressed: firstly toxicity and secondly soft tissue damage. To completely eliminate the toxicity problem, especially for home use, we propose the use of an edible acid which is non-toxic when ingested. The volume of acid for any application in the present invention is limited to several cubic centimeters. After dissolution in saliva the concentration of the acid ingested will drop, and the pH will increase, which is typical for foodstuffs. A typical pH for food acids is 2.5 or more. We have studied the effect of a low pH (<2.5) edible acid on intact enamel. Effects of the pH and temperature on enamel are similar for different edible acids. These effects are illustrated by the dependence of an aqueous acid solution of citric acid, which was found to be the most effective of the edible acids, such as lactic acid, malic acid, tartaric acid, and oxalic acid.

Figure 2:
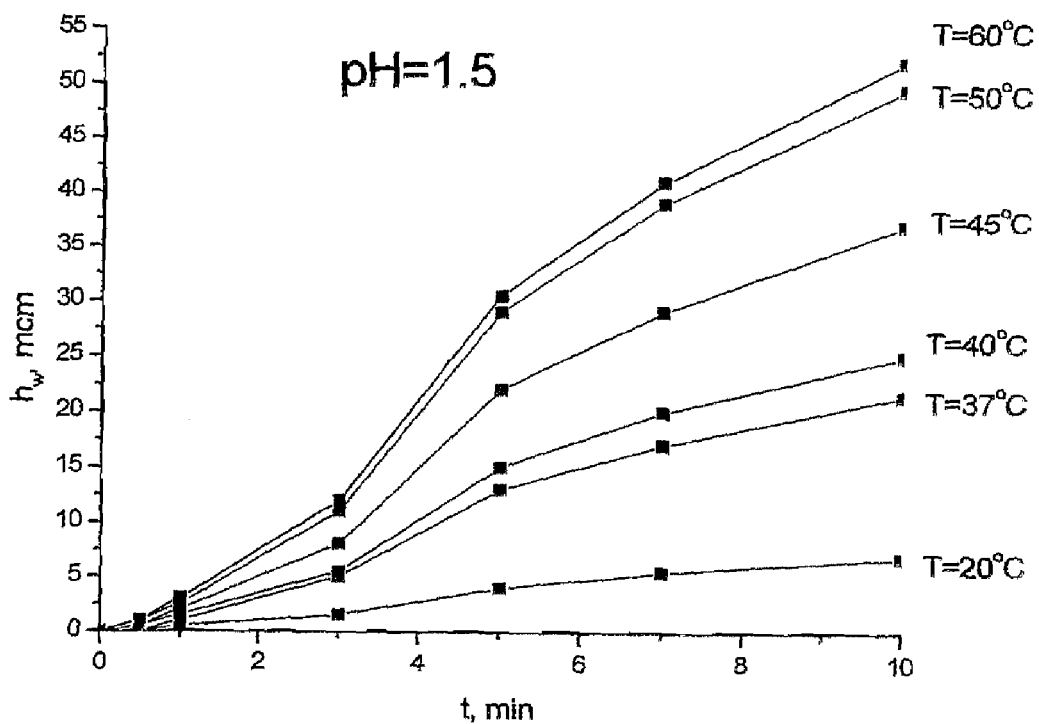
FIG. 2 is a graph showing an etched tooth enamel depth as a function of time at pH=1.5 for temperature T at 20° C., 37° C., 40° C., 45° C., 50° C. and 60° C.
Figure 3:
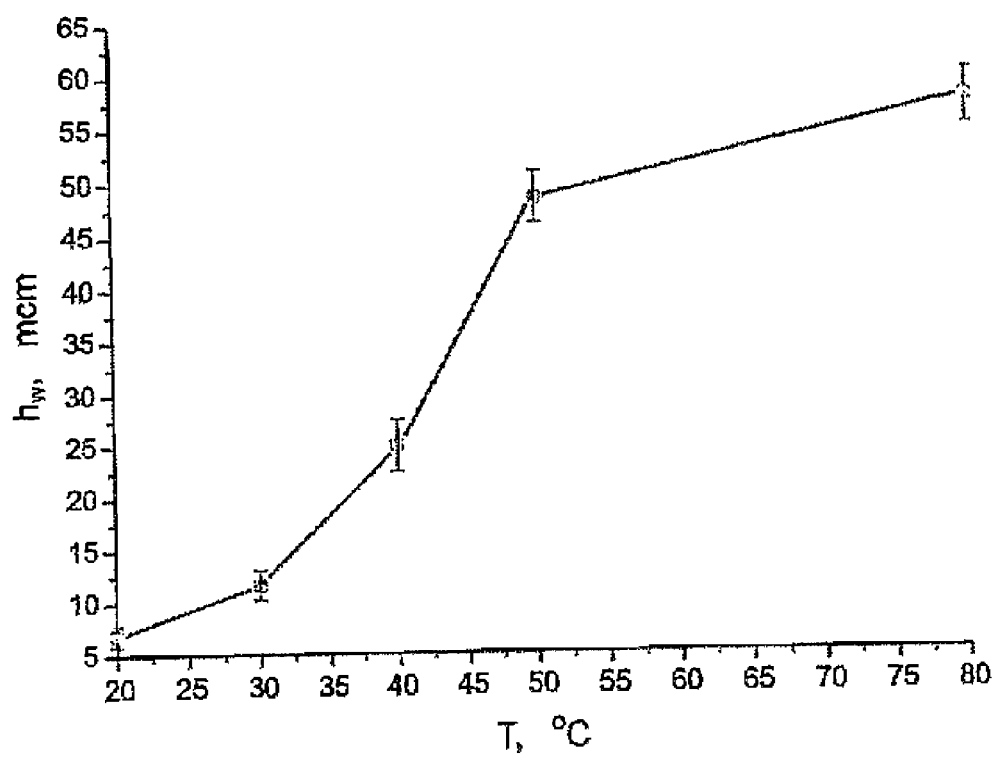
FIG. 3 is a graph showing an etched tooth enamel depth as a function of temperature of an aqueous solution of citric acid at pH=1.5 and exposure time t=10 min.

FIG. 1 shows the relationship between the depth of the enamel layer etched by an aqueous acid solution of citric acid and the pH of the solution. The related FIG. 2 shows the depth of etching as a function of time for different temperatures of the acid. The related FIG. 3 shows the depth of etching as a function of temperature. These graphs illustrate that for rapid etching, it is preferable to use an aqueous solution of citric acid with a pH of approximately 1.5 at a temperature of about 50° C. This is the optimum pH for etching, because increasing the pH above 1.5 and decreasing it of below 1.5 leads to decreasing the effect of etching. Therefore, the most effective pH range is 0.5-5, preferably 0.5-3, more preferably 0.5-2.5, and most preferably 1-1.75.

In examining edible acids, our tests showed that not all acids with a pH ranging from 0.5 to 5 are equally effective as bleaching agents for the removal of stains in enamel. Different acids need substantially different times to achieve the same bleaching effect. A significant factor is the chemical concentration of the acid and its ability to interact with calcium ions, which are the main structural component of hydroxyapatite. For example, tests comparing aqueous solutions of citric acid $(HOOCCH_2)_2C(OH)COOH$ with aqueous solutions of acetic acid $CH_3COOH$ at the same pH and temperature levels showed that the citric acid was more effective. It was discovered that for carboxylic acids, the effectiveness is proportional to the number of carboxylic acid groups. Citric acid has three carboxylic acid groups, whereas acetic acid has only one. An aqueous solution of citric acid is therefore almost 3.5 times more effective in bleaching than an aqueous solution of an acetic acid.

Polycarboxylic acids perform better than monocarboxylic acids, but this benefit does not extend to polycarboxylic acids having hundreds of carboxylic acid groups, because diffusion limits the rate of etching, and the diffusion rate decreases as the square root of the molecular weight of the diffusing agent increases. If the diffusing agent is, for example, a polymeric carboxylic acid, made up of hundreds or thousands of mers, the diffusion rate decreases to such an extent that it is practically negligible. Edible acids found to be effective all have molecular weights of approximately 200 daltons or less (200 daltons is approximately 200 atomic mass units).

The temperature of the acid is another parameter to be optimized for enamel etching when using a high concentration of acid. An increase in temperature increases the depth of etching due to two factors: first, it increases the diffusion coefficient and, second, the rate of the chemical reaction between the acid and the enamel due to Arrhenius law. FIG. 2 shows the depths of etching of enamel as a function of time for the optimum pH=1.5 of citric acid for different temperatures. These graphs can be described by the following formula:

$$K(t) = \begin{cases} \alpha \cdot t, & t \leq t_0; \\ \alpha \cdot t_0 + \alpha_1 \cdot (t - t_0) + \sqrt{D \cdot (t - t_0)}, & t \geq t_0; \end{cases} \quad (1)$$

$$t_0 = 3 \text{ min.}$$

Here, $h_w$ is the depth of the porous layer of enamel in μm after t min of etching as a function of t. Parameters cc, ct, and D can be the functions of both temperature T and pH.

Therefore, for short t (t<3 min) the etching depth is a linear function of time. For longer times, the etching depth as function of time can be described by the square root function, which is typical for the diffusion process. The parameters α, cc, and D were found using the best square fit. Table 1 shows the relationship between the etched layer produced and the temperature, at a constant pH of 1.5.

TABLE 1

Parameters of the equation (1) showing the thickness of the porous (etched) layer of enamel for pH = 1.5 at different temperatures.

| Temperature, ° C. | Parameter | | |
|---|---|---|---|
| | α, μm/min | $\alpha_1$, μm/min | D, μm²/min |
| 20 | 0.524 | 0.158 | 2.604 |
| 37 | 1.751 | 0.515 | 23.124 |
| 40 | 1.921 | 0.469 | 36.801 |
| 45 | 2.767 | 0.833 | 74.738 |
| 50 | 3.755 | 1.31 | 121.664 |
| 60 | 4.124 | 1.504 | 122.528 |

TABLE 2

Parameters of the equation (1) describing the thickness of the porous (etched) layer of enamel for T = 50° C. and a varying pH.

| pH | Parameter | | |
|---|---|---|---|
| | α, μm/min | $\alpha_1$, μm/min | D, μm²/min |
| 2.5 | 0.211 | −0.018 | 0.541 |
| 2 | 1.022 | 0.559 | 4.646 |
| 1.5 | 3.755 | 1.31 | 121.664 |
| 1 | 3.195 | 1.069 | 94.035 |

Using this formula, it is possible to use temperature and time as controls to provide predictable depths of etching of enamel. Therefore, the depth of etching with a low pH edible acid can be up to 50 μm after just 10 minutes of treatment. Such treatment can be performed by a professional. For self-treatment, the maximum etching depth can be up to 5 μm and require a 1.5 minute application time at a temperature of 50° C. FIG. 3 shows that the slope of etching speed vs. temperature is higher in the range 40-50° C. This range of temperatures is preferable for etching with an edible acid.

To avoid such a high temperature, which may be detrimental to the pulpal tissues, and still take advantage of heating, the present invention proposes the use of pulsed heating. Pulsed heating with a pulse width significantly shorter than the thermal relaxation time (TRT) of the tooth (approximately 1-5 seconds) will provide a high peak temperature on the surface of the tooth and a low average temperature in the pulp chamber. The temperature within the pulp chamber is a function of the temperature on the tooth surface, the area heated, the heating pulse width and the duty cycle treatment time. For the heating of a large area of a tooth surface to a temperature $T_{sm}$ with a pulse width shorter than the TRT of a tooth and a duty cycle g, the temperature of the pulp after a long exposure can be expressed as $T_{pm}=(T_{sm}-37)\cdot g+37$. For $T_{sm}=50°$ C., $T_{pm}=42.2°$ C. the maximum duty cycle is g=0.4. The same average diffusion coefficient D in the above formula $T_{sm}=+50°$ C. and g=0.4 is 96 μm²/min, which is 1.7 times higher than the diffusion coefficient for continuous heating with temperature. In conclusion, a safe temperature at which the acid on the tooth surface can be heated, using the pulsed heating method, is up to 50° C., pulse width shorter than 1 sec and a duty cycle g of up to 0.4.

It was discovered, that a high concentration and low pH acid can work well for exposure times long enough to produce significant changes to hard tissue. The use of high concentration, edible acids for treatment of hard tissues is limited by the action of such acids on soft tissues. A series of experiments were conducted, which showed that high concentrations of edible acids can be applied to soft tissues for a period of up to 30 minutes without damaging the soft tissues, which is advantageous in clinical practice as a matter of reducing the cost of treatment. The typical application time for the desired depth of etching can be from 1-5 minutes for home use, and up for up to 10-20 minutes for professional use. The safe treatment time (STT) is defined as the time during which acid can interact with the soft tissues without damaging them. The STT depends on the acid concentration and the temperature, i.e. STT (pH,T), where pH is the pH of the acid, and T is the temperature of the acid. We established this threshold for citric acid with a pH=1.5. The experiment was conducted on subjects with healthy oral tissues. Prior to treatment, the acid was heated to a control temperature T, using a thermostat, and a small volume (approximately $5 \times 10^{-3}$ ml) of acid was applied to an area of the subject's gingival tissue. The thermo-relaxation time of such a volume is approximately 5-10 seconds. To provide for a relatively constant temperature on the tissue surface, the acid was reapplied at the same temperature T to the same area every 5-10 seconds. This procedure was repeated until the subject reported discomfort. A feeling of discomfort always precedes tissue damage. Therefore, the time of the onset of discomfort can be used as an estimate of the STT with a certain safety margin. The results of this experiment are summarized in Table 3.

TABLE 3

The effect of discomfort on gingival tissue as a function of temperature (T) and application time (t).

| min | 1 | 2 | 3 | 4 | 5 | 6 | 7 | 8 | 9 | 10 | 11 | 12 |
|---|---|---|---|---|---|---|---|---|---|---|---|---|
| T, ° C. | | | | | | | | | | | | |
| +20 | – | – | – | – | – | – | – | – | – | – | – | + |
| +36 | – | – | – | – | – | – | – | – | – | + | | |
| +50 | – | – | – | – | – | – | – | + | | | | |
| +70 | – | – | – | – | – | + | | | | | | |
| +90 | – | – | + | | | | | | | | | |

"–" means that the subject experienced no discomfort,
"+" means that some discomfort was reported.

These experiments showed that even using high concentrations and high temperatures (up to 90° C.), citric acid did not cause damage to soft tissues. These experiments also showed that when citric acid at temperatures of 50° C. and a pH of 1.5 was used, the STT was greater than 8 minutes. Therefore, within these parameters citric acid can be used for the treatment of hard tissues without the risk of damage to soft tissues for a period of about 8 minutes.

While not wishing to be held to any theory, reduction of depth of etching at pH levels less than 1.2 may be related to the reduction of the diffusion properties of the aqueous acid solution due to its increased viscosity. Increasing the temperature of the solution to greater than 50° C. is undesirable because of a risk of damaging the pulp of the tooth. Nevertheless, certain conditions, like a reduced treatment time interval, can allow an increased temperature. From the presented graphs, it can be seen that by the action of citric acid at 50° C. and pH=1.5, the etched depth of the tooth enamel is 40 µm. If this depth is, from a practical point of view, insufficient to achieve the desirable clinical or cosmetic effect the application can be repeated several times.

Control of etching using highly concentrated edible acid can be achieved by using different additives. The interaction between acid and hard tissue leads to a dissolution of mineral components and modification of organic components. Three types of dissolution are known: Type I, where enamel rods are removed preferentially, Type II, where the organic matrix is removed preferentially, and Type III, where both Type I and Type II dissolution take place. The different types of tooth rejuvenation processes require a Type I or a Type II etching pattern as discussed below. The present invention, proposes to control the etching process, using edible acid with a special additive. One of control mechanisms involves additives, including, but not limited to, the ions of Ca Cr, Ba Cd, Mg, P, SiF, and their compounds, such as $PO_4$. Other non-organic or organic additives may also be used. Additions of such ion combinations may slow the dissolution of the inter-prismatic regions or may provide for re-crystallization of hydroxyapatite crystallites, or the building of new crystallites of fluroapatite. The use of such additives can be effective in the control of tooth etching, or in the preparation of the tooth surface for the application of a protective or cosmetic coating, or for the thermal re-crystallization of the tooth surface. In the present invention, we demonstrated this effect, using a composition of citric acid and a solid mixture of potassium (K), calcium hydroxide $(Ca(OH)_2)$, magnesium (Mg) and phosphoric acid $(H_3PO_4)$. This compound uses the ratio "water:citric acid: mixture"=5:1:1 to obtain a compound with a pH=1.5.

Extracted teeth with healthy enamel were used in the experiment. One half of enamel surface of each tooth was covered with a protective cover ("control side"). The other side ("treatment side") was left unprotected. The gel was applied for a period of six hours to the treatment side of the tooth, and citric acid was applied for a period of six hours to the treatment side the other tooth at a temperature of +24° C. After six hours, the tooth exposed to citric acid had completely lost its specular reflection property and was easily damaged by scratching with a dental probe. The surface of the tooth in the gel retained its specular reflection property, and the hardness on the treatment side was marginally lower than that of the control side. In addition, the whitening effect of both treated sides was comparable. The results can be explained as follows. In the case where the tooth was exposed to citric acid, the predominant etching was of the enamel prisms (Type I etching), and in the case where the tooth was exposed to the gel, the predominant etching was of the enamel prism sheaths (Type II etching).

In a further experiment, a tooth had half of the surface exposed to an aqueous solution of citric acid and the other half to the gel. Both the citric acid solution and the gel had a pH=1.5 and a temperature of +20° C. Exposure in both cases was for 180 minutes and the tooth was then washed in distilled water. A strong whitening effect was observed for both sides of the tooth. The tooth was then exposed to an aqueous solution of methylene blue. The citric acid side was colored by methylene blue and the side coated with the gel showed only minimal coloration.

This result proved that exposure to citric acid leads to Type I etching of enamel and forming a highly porous structure, which could be easily colored by molecules of ethylene blue. In contrast, the abovementioned gel-like compound led to Type II etching, resulting in a low porosity structure of enamel surface.

In addition to choosing the acids, and correctly formulating the composition, it is also necessary to add chemicals, which minimize etching of hydroxyapatite and fluorapatite. These include compounds such as calcium chelating agents, which aid by chemically removing active calcium ions from the etching agent. One such agent is ethylenediaminetetraacetic acid (EDTA) and its salts. This material is currently widely used in dentistry for treating cavities and root canals before filling. The addition of EDTA and similar compounds in correct proportions into the etching compound, which is an aqueous acidic solution with a pH of 1.2 to 5, can significantly improve the present method.

A non-toxic etching compound for selective etching of part of the enamel, including stain and/or weak components of enamel, such as carbide apatite and defective micro crystals of hydroxyl apatite, are proposed in the present invention. Such a compound a comprises an edible acid with a pH in the range of 0.5-5, preferably 0.5-2.4, and most preferably 1-1.75, with ions from the following list: Ca, Cr, Ba, Cd, Mg, P, As, Si, F. These ions can be in a chelating agents, such as EDTA or as the salts NaF, $CaPO_4$, or $Ca(COs)_2$. For better whitening effect, stain bleaching components, such as peroxides, can be added to an edible acid based compound. Etching of enamel by such compound can create channels for better penetration of the bleaching components, such as peroxides, to the stain.

In the present invention, all etching compounds described above were based on edible acids and can be used for tooth rejuvenation including tooth whitening. These compounds can be used at a temperature higher than tooth (body) temperature (37° C.). Additional additives can be mixed with these compounds to improve heating. These include molecules or particles with strong light absorption characteristics in a predetermined spectra of light, for example carbon particles. A molecule-induced exothermic chemical reaction could also be used. The tooth rejuvenation compound can be applied to the tooth as a gel, toothpaste, within a strip, in trays, in soft material impregnated with the compound, as a rinse or as a part of a drink or special food. The rejuvenation compound may also contain flavors and sweeteners to make it more palatable.

Tooth Rejuvenation Method and Apparatus

In the present invention we suggest a method of tooth rejuvenation, which includes deep cleaning of the hard tissue surface (e.g. enamel, dentine, or cementum), consisting of mechanical cleaning of the tooth surface to remove biofilm, followed by a deep cleaning by tooth rejuvenation compound based on a acid, followed by optional mechanical cleaning, followed by remineralization of enamel, utilizing the natural properties of saliva and/or by remineralizing via rinsing, strip(s) or mouth tray(s), which contain remineralizing compounds, such $CaPO_4$, fluoride and others. This method is based on the fundamental property of crystalline growth, i.e. that the fastest and most defect-free crystal growth takes place on an ideally clean crystal surface. Defect-free crystals have maximum chemical stability. Enamel remineralization involves growth of hydroxyapatite or fluorapatite crystallites from a saturated aqueous solution of Ca and $PO_4$ ions (obtained from saliva) or fluoridated water. A major requirement for crystal growth is a clean crystallographic plate. Under normal conditions, enamel is covered by a biofilm and a pellicle. The presence of these organic substances complicates the remineralization process significantly. Both biofilm and pellicle can be removed by mechanical cleansing, such as brushing with abrasive toothpaste. However, following such cleaning, the enamel surface still contains micro-particles, molecules and molecular clusters, referred to as residual dental film. Particles in the residual dental film are smaller than the abrasive particles and, as such, cannot be removed by mechanical cleaning. These particles can however, be removed chemically, by way of dissolution or destruction of the residual dental film. The current invention proposes the use of a tooth rejuvenation compound based on highly concentrated acid for such chemical cleaning. The compound is applied to the tooth surface for a controlled amount of time, sufficient for the removal of the residual dental film, but short enough to avoid significant destruction of enamel. This time depends on the acid concentration and compound temperature. For a highly concentrated acid, such as citric acid, with a pH in the range of 0.5 to 5, preferably 0.5-2.5 and most preferably 1-1.75, the application time would be from 5 seconds to 10 minutes at the body temperature within the oral cavity. At a temperature of 90° C., this time can be decreased to within a range of 1 second to 2 minutes. The preferred temperature is in the range of 38-50° C. The most effective and safest is within the range of 42-50° C. The temperature of the compound can be altered so that the temperature pulse is shorter than the thermo relaxation time of the tooth and the duty cycle of heating is within the range of 40-100%.

The tooth rejuvenation compound may be applied using one of the devices described below, or by a spray or brush, or by a film applicator soaked with the bleaching compound. It can also be applied onto the teeth directly as gel, gel in a tray, or a film applicator, such as a strip or film from a soft material. In the case of a film applicator, it can be cut to fit the shape of the teeth. When using a film applicator, the rejuvenation compound should be sufficiently viscous, which can be accomplished using various fillers. These can be lipid-based fillers, with phase transition from crystallized form to liquid form within the temperature range of 30-85° C. Most lipids, including edible lipids, present at room temperature (17-30° C.), exist in crystallized form and will melt upon contact with the tooth because the temperature of the tooth is approximately 37° C. An electrical current, heat or irradiation with the appropriate wavelength and power, may be used to initiate a phase transition to a lower viscosity. This procedure may be repeated several times during one treatment phase, and several such treatment procedures can be performed on the teeth during one appointment. To increase the effectiveness of the tooth rejuvenation compound, it is recommended that its temperature to be in the range of 42-50° C. at the application site. It is possible to heat the tooth rejuvenation compound by irradiating it with a radiation at a wavelength, which is well absorbed by the compound.

Since the dependence on temperature is non-linear, pulsed heating is recommended. Pulsed heating applies short heating impulses up to 60° C., allowing for intervals of cooling. Using pulsed heating, the average temperature to which the tooth is heated is within allowable limits, but the effectiveness of bleaching increases. A semiconductor or a non-coherent light source in the red or near-infrared (600-1350 nm) part of the spectrum, which corresponds to minimal absorption by the surrounding soft tissue of the mouth, may be used as the heating source. A light absorbing ingredient could also be added to increase light absorption higher than that of surrounding tissue, e.g. small particles of carbon, including nanoparticles as fullerenes or astrolens. Such a light absorbing ingredient would absorb light in the range of wavelengths different from that of the high light absorption of surrounding tissue. The size of the carbon particles can be from several angstroms to hundreds of microns.

At the end of the treatment, after removing the bleaching compound, it is recommended that the tooth enamel be heated to achieve an additional rejuvenation effect and to remove tooth rejuvenation compound from the inner pores of the teeth by evaporation. The same light absorbing particles could be used as a part of the remineralization compound. For thermal activation of this compound, the light heating devices, described in detail below, can be used.

After bleaching, the tooth should be washed with water spray or with a liquid with a pH greater than 5.5 or by rinsing the mouth to remove the tooth rejuvenation compound. This cleaning phase may also be combined with a mechanical cleaning phase, by adding abrasive particles, such as silica, quartz, etc. to the tooth rejuvenation or cleaning compounds.

The acid-based compound may be applied to the teeth in different ways. For example, the compound may be applied using a mechanical tooth brush with vibrating bristles (electro-mechanical toothbrush or sonic toothbrush) or a tooth polisher with a flexible rotating tip or others devices, described in detail below.

Immediately after this procedure, crystal growth begins on the cleaned crystal surface due to the remineralizing effect of saliva, with the development of a hydroxyapatite or fluroapatite coating. Unlike the natural process of remineralization, the growth happens more rapidly and results in better bonding to the original structure of enamel. In the natural conditions, development of such a coating is complicated by the process of biofilm and pellicle formation. The current invention proposes rinsing and/or application via an intraoral tray with a sterilized mixture of Ca, $PO_4$ or F ions, with an optional addition of anti-bacterial additives. The duration of application may be from 1 second to 1 hour. Remineralization can also be achieved using chewing gum, containing Casein Phospho Peptide-Amorphous Calcium Phosphate (CPP-ACP) nano-complexes or by using $NaF_2$, $Ca(CO_3)_2$, and acidulated flourophosphate gel (e.g. Phos-Flur®). In another embodiment, strips may be used, comprising of a polymer film with a viscous coating, which contains Ca, $PO_4$ or F ions. Such a strip may be kept on the tooth surface for a considerably longer period of time, from 10 minutes to several hours. In another embodiment, gel with a remineralizing composition in special trays could be used. The procedure may be conducted in both the professional and the home settings.

Remineralization process can take place simultaneously with demineralization of hard tissue via interaction of the hard tissue with rejuvenation compound. The rejuvenation compound containing an edible acid with additives, including, but not limited to, Ca, Cr, Ba, Cd, Mg, P, As, Si, F or other elements, can provide control of balance between remineralization and demineralization processes in real time.

As a result of treatment with acid based compound, a porous layer can be created on the tooth's surface. The depth of such porous layer and spatial distribution of its porosity can be controlled by the additives in the compound, temperature and treatment time. For example, the depth of the porous layer may vary from 0.1 micron to 100 microns. The porosity may be uniformly distributed vs. depth or be maximum on the surface or inside the layer.

Rejuvenation of tooth structure in its superficial layers of hard tissue using the tooth rejuvenation compound could substantially improve the esthetic appearance of teeth. The main mechanism is removal of stains accumulated in this layer by a highly concentrated acid.

In the professional setting, the tooth rejuvenation compound is applied by an operator (e.g. dentist, hygienist, or a beauty therapist). The depth of tooth surface etching can be from 0.5-100 µm per treatment, depending on the initial condition of the enamel and the goal of treatment. Following cleaning, teeth are rinsed with water or cleaning compound to remove residual tooth rejuvenation compound or increase its pH. After rinsing, the cleaned enamel surface is remineralized by the application of compounds, which promote the growth of enamel crystals by rinsing with the aforementioned compounds, or by the application of these compounds via mouth trays and/or strips. For a better protective and cosmetic effect, these procedures may be followed by the coating of the etched/modified hard tissue surface with controlled heating using laser, as described in detail below. For application by a professional, the time frame involved may be up to 10 min at a temperature of 40-50° C.

Ia the home setting, the tooth rejuvenation compound can be applied by the consumer as a part of daily brushing. The depth of tooth surface etching would be from 0.1-5 µm per treatment. A porous layer of so minimal a depth would be remineralized between tooth brushing episodes. The period of application for home use would be up to 3 minutes at the body temperature of 37° C. and up to 1.5 minutes when the compound is heated to a temperature of 50° C.

Devices for Treatment

The method of tooth rejuvenation with the tooth rejuvenation compound can be practiced with different devices.

Figure 4:
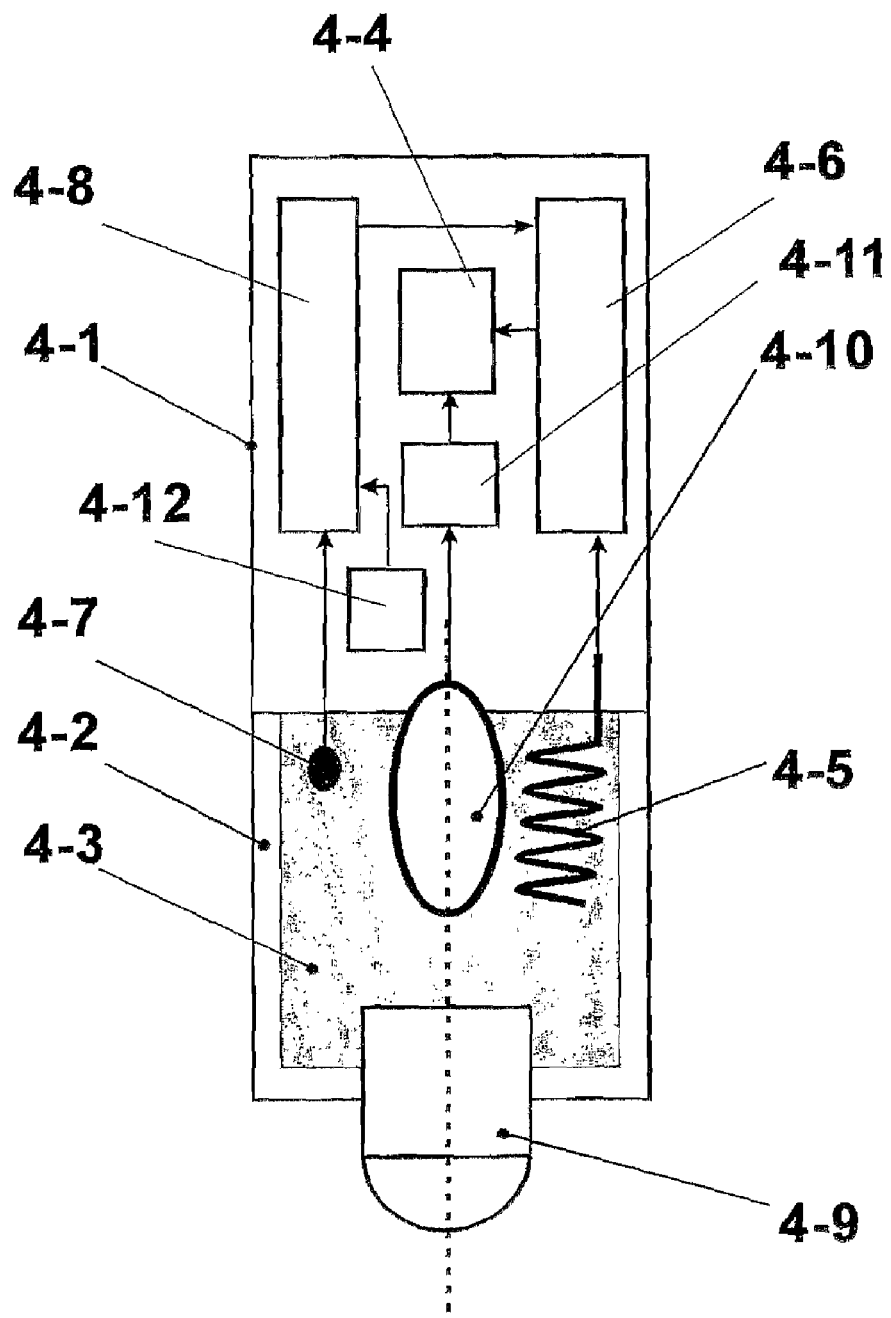
FIG. 4 is a schematic illustration of one of the embodiments of a hand-held device.

The handheld device shown in FIG. 4 is one possible embodiment and is not intended to be limiting in any way. The device comprises of a housing 1, designed as convenient to hold. Inside housing 1, there is a capsule 2, containing a tooth rejuvenation composition 3. In addition to capsule 2, there is an electrical power source 4, which can be a battery or a rechargeable battery, and a heating element 5, located within capsule 2, coupled to power source 4 through a switch 6: A temperature sensor 7 is also enclosed inside capsule 2, and is electrically coupled to switch 6 via a control system 8. Tooth rejuvenation composition 3 is delivered to the tooth surface from capsule 2 by a delivery system 9. As an alternative or as an addition to the Ohm-like heating element 5, light heating sources may be used. Light source 10 emits light energy in the spectral region most effectively absorbed by the compound, applicator or tooth. Light source 10 may be a light emitting diode LED, or a semiconductor laser or lamp and is coupled power source 4 via a switch 11 and an indicator lamp or LED 12, electrically connected to power supply 4 via control system 8.

This device functions as follows. The operator or a user activates heating element 5 or light source 10 with switch 6. Heating element 5 is enclosed inside capsule 2 with tooth rejuvenation composition 3. Once the desired temperature of composition 3 is reached, temperature sensor 7, coupled to control system 8, activates indicator 12, turning off heating element 5 or light source 10 the device is now ready for use. During the procedure, control system 8 controls the temperature of composition 3 by periodically turning heating element 5 on and off as necessary. Composition 3 is deposited onto the enamel surface via applicator 9, which can be made of a porous material, such as foam, or a fibrous material.

Applicator 9 made from such a material limits the amount of composition 3 deposited on the tooth surface. It is necessary to maintain the temperature of composition 3 already deposited on to the enamel surface, light source 10 can be activated by switch 11. The radiation is partially absorbed by composition 3, by the underlying enamel or by the material of applicator 9, which would preferably be made from porous bristles whose capillary action would deliver composition 3. The applicator can be made from a material, which can absorb light energy from the wavelengths used to heat the compound. The temperature achieved would be up to 90° C. in the pultie mode with a pulse shorter than the thermorelaxation time of the tooth and a duty cycle of 40-100%. The composition can be preheated in capsule 2 to a temperature of 40-60° C. and additionally heated in applicator 9 as well. The temperature of the composition, tooth surface and soft tissue in contact with the tip of the applicator would ideally be in the range of 40-50° C. To control this temperature, a thermosensor can be incorporated into the applicator 9; e.g. a thermistor or thermocouple, placed into one of the bristles. The signal from this thermosensor through control system 8 can regulate the power of light source 10 to keep the temperature of the compound on the tooth within a predetermined range. For better delivery of composition 3 to applicator 9, a compression mechanism could be included in the device. One such embodiment could be that capsule 2 be made from a flexible material and compression is provided by hand pressure. Alternatively, a plunger mechanism could be included in the device. Capsule 2 could be a disposable component for single use or reusable, requiring refilling for every treatment.

Figure 5:
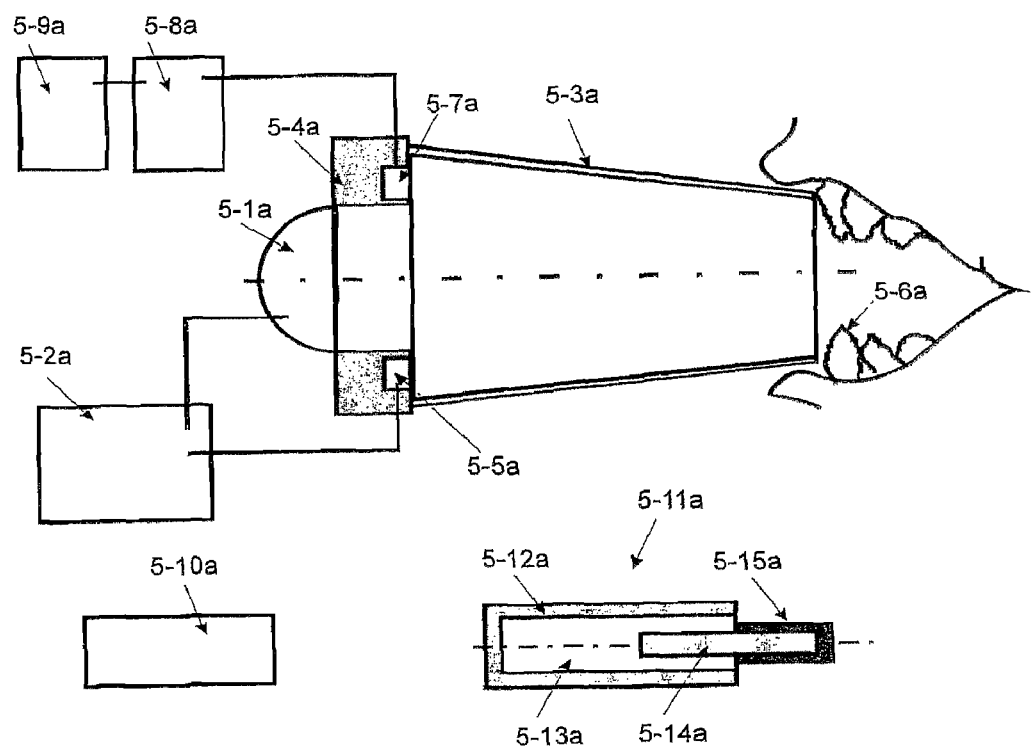
FIG. 5 is a schematic illustration of one of the embodiments of a device mounted in the mouth.

An alternative device is shown in FIG. 5. This device is better suited for the treatment of anterior and some posterior teeth. It comprises of a light source Ia, a control power block 2a, a detachable mouthpiece 3a, coupled to a light source via a connector 4a. The light sources can be a lamp, a filtered lamp or a semiconductor source such as a LED or diode laser. The light source is equipped with an optical system to provide uniform distribution of light onto treated teeth. The wavelength of the light can be selected from a range of wavelengths with a ratio of coefficients of absorption of the compound and surrounded tissue of more than 1. For example, it could be in the range of 600-1350 nm if carbon particles are used as the chromophore for the compound. The device also comprises of a temperature sensor 5a, which measures the surface temperature of the tooth surface and the compound 6a. An optional television camera 7a, with an optical system is coupled to its own power source 8a and display screen 9a. An applicator 10a contains the tooth rejuvenation composition 13a in the form of a film or strip. The strip or film can be made of several layers, with one layer saturated with light absorbing particles, fiber, fabric, e.g. carbon fabric, or other material. The applicator (compound distributor) 11a can also be used as a reservoir 12a containing a brush 15a for the application of the compound 13a to the enamel by a delivery system 14a. The delivery system 14a is made of a porous material and contains a brush 15a for the application of the compound 13a onto the tooth surface. To use the described device, compound 13a is delivered by delivery system 14a onto surface of the teeth 6a. Brush 15a deposits composition 13a onto the tooth surface, then detachable mouthpiece 3a is inserted into the patients mouth. Mouthpiece 3a is coupled via connector 4a to light source Ia, temperature sensor 5a and television camera 7a. Light source Ia heats composition 13a to the optimal temperature, controlled by temperature sensor 5a. Once the optimal temperature is reached, light source Ia is turned off or decrease power. Heated composition 13a etches the enamel precisely to a controlled depth. Upon completion, the device is turned off, mouthpiece 3a is removed and the enamel washed with water. In an alternative version of the device, sensor 5a or camera 7a may incorporate a device, such as a spectrometer or a spectral camera, to measure the pH of the compound or its levels of Ca or P and their ratio.

Figure 8:
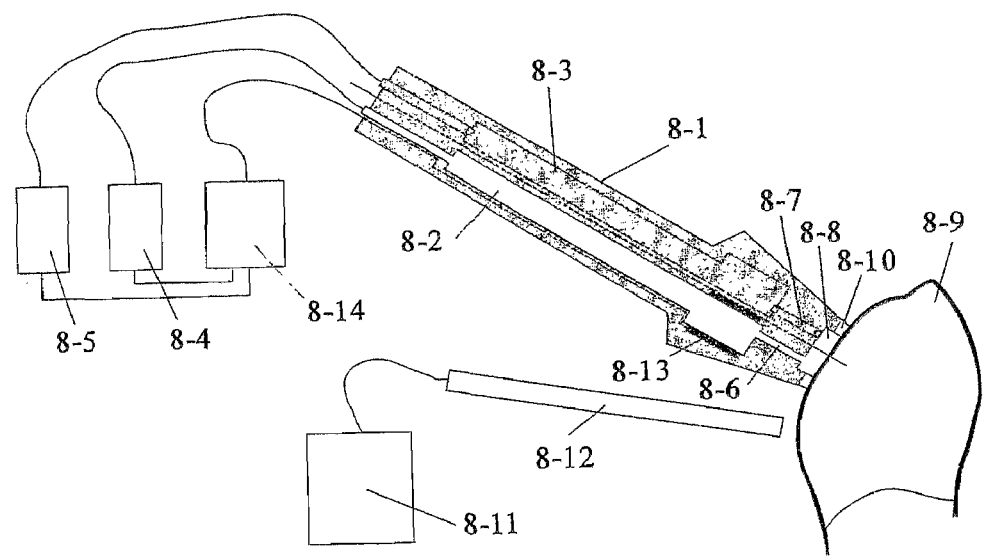
FIG. 8 is a schematic illustration of another embodiment of a hand-held device.

Another embodiment is shown in FIG. 8. The device allows the compound to move along a processable surface (enamel), which results in removal of the boundary layer between the compound and the enamel, which in turn reduces the speed of diffusion of compound components onto the hard tissue and therefore complicates the process of rejuvenation. The device consists of a handpiece 1 in which the tank with a composition 2, and tank with water or remineralization compound 3 are located. The tank with composition 2 is connected to a pump 4, and the tank with compound 3 is connected to a pump 5. The composition from tank 2 is put under pressure from the pump or plunger mechanism 4 and expelled via a channel 6 to a target chamber 8. Water from the tank with remineralization compound 3 under pressure from the pump or plunger mechanism 5, is also expelled into chamber 8. The mixture of water and acid reacts and, under the pressure from pumps 4 and 5, leaves chamber 8 through channels 10. Chamber 8 is in contact with tooth surface 9. Any excess mixture, which reaches the oral cavity, can be removed by the standard suction systems available in dental surgeries for saliva removal (11, 12). The tooth rejuvenation in tank with composition 2 can be heated by a heating system heating 13. Pumps 4, 5 and heating system 13 are connected to the control and supply mechanism 14, which can be located in handpiece 1, as shown in the main unit.

Figure 9:
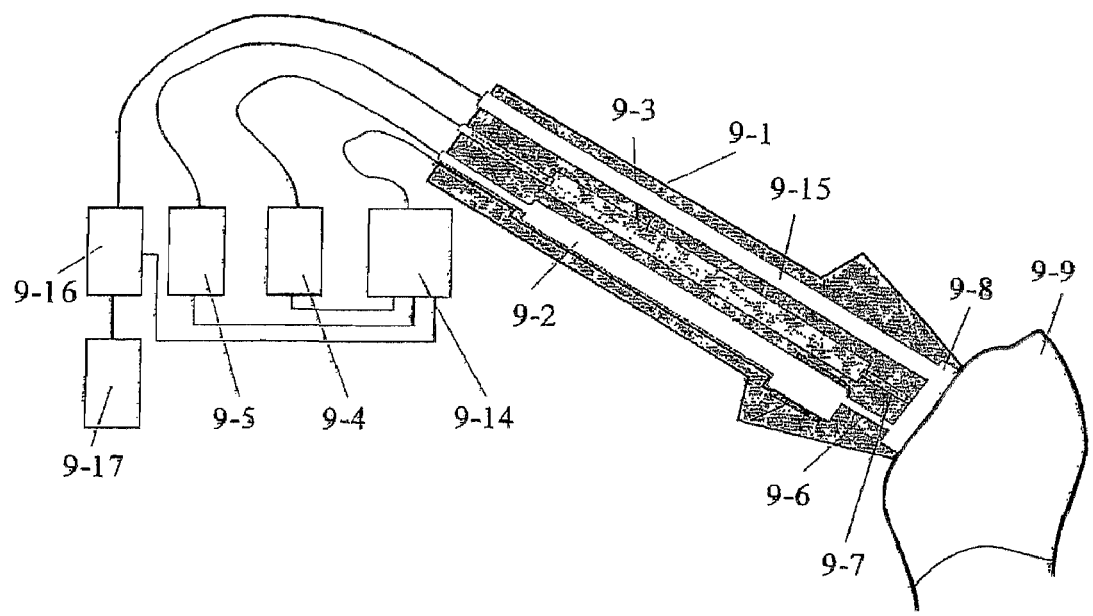
FIG. 9 is a schematic illustration of yet another embodiment of a hand-held device.

A variation of this device is seen in FIG. 9. This device differs from the above-described device in that it contains a mechanism for the removal of the tooth rejuvenation compound from the target area 9 into a replaceable tank 17. This occurs by suction in the duct 15, created by a compressor 16.

Further variations to the device are shown in FIGS. 8 and 9. It contains a one-way valve between tanks with composition 2 and remineralization compound 3. Another variation comprises of a plunger mechanism, which causes pressure to be applied to tanks with composition 2 and remineralization compound 3, with valves between the tanks and the target area 9. The devices shown in FIGS. 8 and 9 can provide full control of the interaction time between the tooth rejuvenation compound and the teeth and, as a result, can provide precise control of the depth of hard tissue etching. The device can operate in the pulsed mode, with a pre-programmed cycle of operation. Firstly, the preheated compound from tank with composition 2 is released onto the tooth surface for a predetermined period of time. Secondly, the water or remineralized compound form tank with remineralization compound 3 is released onto the tooth for a predetermined period of time. The cycle can be repeated. With this device, the exposure time of the compound to the tooth surface can be very precisely controlled. Because the compound proposed for use with this invention is edible and non-toxic, any excess material, which escapes into the oral cavity, can be swallowed or removed with standard dental evacuation system.

Due to the high margin of safety and lack of toxicity, the procedure may also be used in the home environment without professional supervision. In this variation, the method would be most effective as a part of the regular oral hygiene procedures. Here, the patient cleans his or her teeth with a regular toothbrush or special mouth piece and toothpaste, and follows with cleaning using a toothbrush and tooth paste containing an edible acid, such as citric acid, rinses, and then can supplement the procedure with the use of strips or trays with the rejuvenation compound. Any acid-based compound remaining on the teeth may have the undesirable effect of uncontrolled demineralization of the enamel surface. In the professional setting, this issue is resolved by rinsing of the enamel surface with water under supervision, or by professional staff using appropriate water syringes.

The present invention proposes the use of a multi-cycle tooth rejuvenation process. One cycle would involve treatment with tooth rejuvenation compound, followed by treatment with remineralization compound. The cycle can be repeated for up to 20 times. The amount of compound delivered in every cycle contains a small volume, and saliva, with its pH of more than 5, would neutralize and dissolve the acid. Such a solution has low etching effect on hard tissue. The amount of compound delivered in each cycle preferably should be lower than 0.25 cm³. In the home setting, cleaning of teeth and gum from acid with a water-based solution may be enforced in the following three ways.

Firstly, the rinsing may be enforced through the use of a timer. The timer self-activates after a given period of time, informing the user that it is necessary to rinse with water. Such a timer could be used for both the at-home and in-office treatment.

Figure 6:
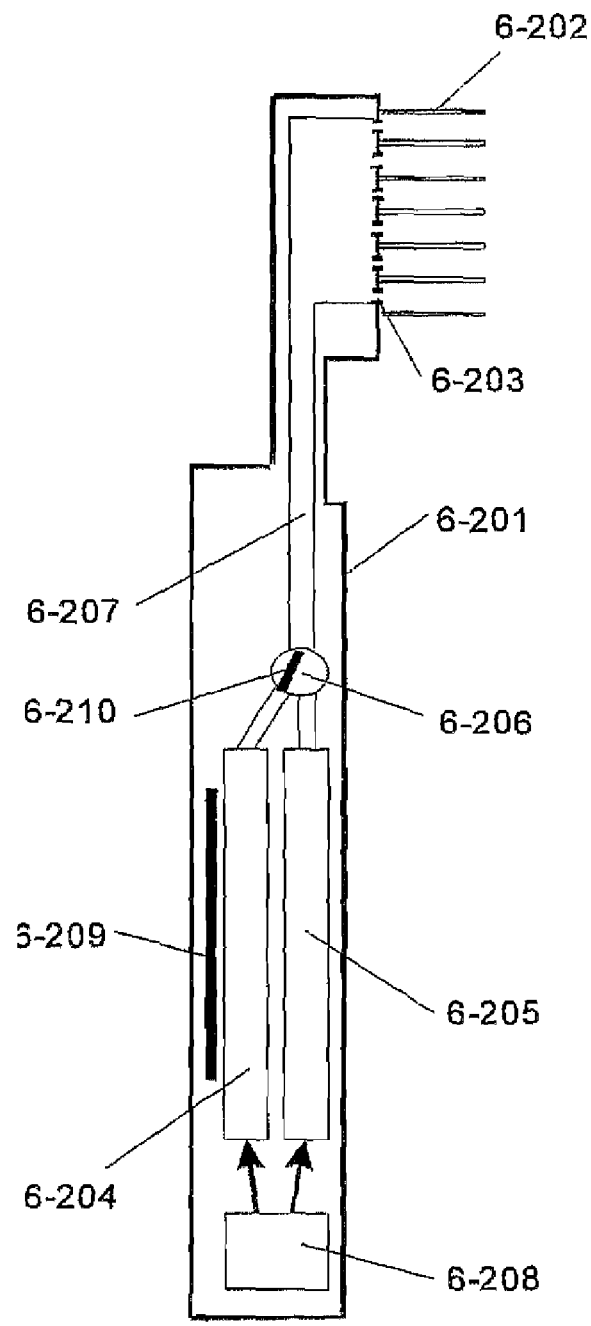
FIG. 6 is a schematic illustration of one of the embodiments of a home-use device.

Secondly, a device exclusively for home use is shown in FIG. 6. It can be a mechanical, light emitting or electrical toothbrush, which can also be used for normal daily brushing. It contains an automatic mechanism for releasing an acid-based compound, and a water based solution as described below. The acid based-compound is stored in chamber 204. The compound may contain additives such as the abrasive particles, e.g. silica, quartz etc, as well as other antibacterial particles. The water-based cleaning solution is stored in chamber 205. In addition to water, the solution may contain remineralizing agents, such as $CaPO_4$, fluoride, abrasive particles, etc. The acid-based compound is heated by a heating-element 209. An electric motor 208 is used to initiate delivery of each substance via a valve 210, a delivery tube 207, and brush ducts 203 into the user's oral cavity. Bristles 202 provide for the brushing action. These components are enclosed within, or attached to the toothbrush body 201. During brushing, the electric motor initiates the automatic release of the acid-based compound and water-based solution, in an alternate fashion by switching between two positions of the valve membrane 206.

Figure 7:
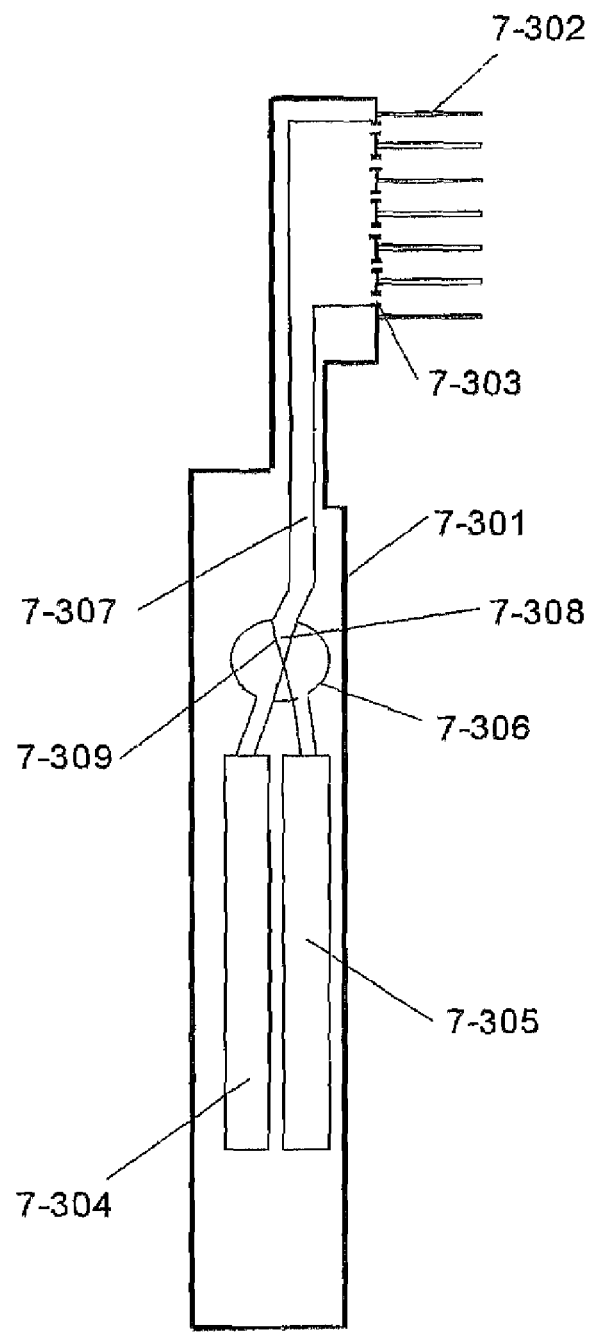

Thirdly, a different version is a manual toothbrush, as shown in FIG. 7. The toothbrush contains a manual mechanism for releasing an acid-based compound and a water-based cleaning solution, as described below. The acid based-compound is stored in a chamber 304. The compound may also contain abrasive particles, such as silica, quartz etc, or anti-bacterial medicaments. The water-based solution is stored in chamber 305 and may contain remineralizing agents such as calcium phosphate, fluoride, abrasive particles etc. In addition to water, the solution may also contain remineralizing particles, such as $CaPO_4$, fluoride, and others. Each substance is delivered into the oral cavity via a valve 306, delivery tube 307, and brush ducts 303. Bristles 302 provide for the brushing action. All these components are enclosed within or attached to the toothbrush body 301. During brushing, the user manually initiates release of the acid-based compound and water-based solution, in an alternate fashion, by applying pressure to the body of the toothbrush. The applied pressure causes the membrane to move alternatively, between positions 308 and 309, leading to selective blocking of the substance contained in chamber 304 or 305, but not both. As a result, a measured dose of acid-based compound is delivered to the tooth surface during one pressure application, which this is removed by the water-based solution during the next pressure application. Consequently, only a small amount of acid remains on the tooth. This amount is within the safety margin for the soft tissues because it is either removed by water or is dissolved in saliva, due to its washing action and higher pH.

Devices shown on FIG. 4-FIG. 9 may be equipped with a source of therapeutic light, including, but not limited to semiconductor light sources or lamp. These light sources can provide bacteria reduction effect, photobiostimulation effect, or pain reduction effect during tooth rejuvenation treatment.

Example 1

In-Office Tooth Whitening Treatment

An in-office clinical case is described below, which demonstrated the efficacy and safety of tooth whitening using the tooth rejuvenation compound proposed in present invention.

Materials and Methods:

1. The study was carried out on the maxillary right first premolar, maxillary left first premolar, and mandibular right first premolar of a 25-year old female subject.
2. The teeth were then mechanically cleaned, using a flour of pumice and water mix on a bristle brush in a slow speed handpiece.
3. The VITA shade guide was used to evaluate the shade prior to treatment, after treatment, 1 week after treatment and 1 month after treatment. The results were recorded using digital photography.
4. A water-based solution of citric acid with a pH=1.5 and temperature of +70° C. was applied to the subject's enamel using a brush. The compound was applied for a period of 10 minutes to one half of enamel surface (treatment side), with the other half, covered by a protective material acting as the control side. The application consisted of a series of repeated cycles throughout the 10-minute period. Each cycle consisted of a 5-second application of the compound, followed by a 10 second pause, with the total of 40 cycles. Throughout the treatment, the average temperature of the solution on tooth's surface was +50° C.
5. The treated teeth were left intact in the subject's mouth for a period of one month, after which they were extracted for micro-hardness testing and SEM evaluation.

Results:

1. Throughout the treatment, the subject did not report any pain or discomfort.
2. No change in gingival tissue and no hypersensitivity were observed after treatment or during follow up appointments.
3. Immediately after treatment, the treated sides showed a whitening effect as shown in Table 4. A clear demarcation line was observed in every tooth between the treatment and the control sides, with a superior whitening effect observed on the treatment side. The treatment side was less glossy than the control side. The whitening effect on the treatment side and the demarcation line were still observed, although progressively less, at one week and one month after treatment. The gloss progressively returned to the tooth surface on treated side.

Conclusions:

The results showed that the use of whitening compound, based on an edible acid with a pH=1.5 and a temperature of 50° C., when applied for a period 10 min to non-severely discolored teeth (A2-A2.5), produced an immediate significant whitening effect with no discomfort to the patient, no damage to the soft tissues, and no post treatment hypersensitivity. The partial loss of surface gloss observed initially, was restored within one week after treatment.

TABLE 4

Shade of the teeth as assessed using the VITA shade guide.

| | VITA Classical Shade Index | | |
|---|---|---|---|
| Tooth # | Pre-treatment, before mechanical cleaning | Pre-treatment, after mechanical cleaning | After treatment |
| Maxillary right premolar | A2.5 | A2 | A1 |
| Maxillary left premolar | A2.5 | A2 | A1 |
| Mandibular right premolar | B2 | A2.5 | A1 |

Example 2

At-Home Tooth Whitening Treatment

A home-based clinical case is described below, which demonstrated efficacy and safety of tooth whitening using the tooth rejuvenation compound proposed in present invention.

Materials and Methods:
1. The subject was a male volunteer, with healthy mucosa and gingival tissue as determined by an experienced clinician.
2. The study was conducted on the maxillary right central incisor. Like the remainder of subject's anterior teeth, it was stained due to natural causes, such as heavy smoking and coffee drinking. Prior to the start of treatment with the rejuvenation compound, the subject was instructed to perform intensive brushing of anterior teeth, with regular toothbrush and toothpastes for the duration of one week.
3. A water-based solution of edible citric acid was used with a pH=1.5, at room temperature.
4. The solution was applied to the tooth surface using a toothbrush on daily basis before sleep, for a period of 2 minutes.
5. After the application of the acid based compound, the teeth were brushed in the regular manner using "Blend-a-med Pro-mineral action" anti-caries toothpaste (Procter & Gamble) according to the manufacturer's instructions.
6. The treatment was performed daily for the period of three weeks.
7. For the next four months, following the three weeks of treatment, the subject brushed with "Blend-a-med Pro-mineral action" toothpaste in the standard manner.
   Evaluation technique included: examination of the gingival condition, hypersensitivity test, clinical photography and measurement of the optical coefficient of reflection of the tooth on computer-simulated white color. Teeth were photographed with a digital camera (MINOLTA DiMAGE 7i) in automatic mode with resolution of 2560×1920 pixels. The photographs were taken before and after treatment, with the distance, light conditions and camera zoom all held constant.
8. Evaluation was performed before treatment, upon completion of treatment, and one month and four months after completion of treatment.

Results:
1. Throughout treatment the subject did not report any pain or discomfort.
2. No dentinal hypersensitivity was reported by the patient, nor any change in gingival tissue was observed by the clinician after treatment, or during the review appointments.
3. The above three-week treatment regiment, using an aqueous solution of edible citric acid for the duration of three weeks, significantly improved both the esthetic appearance of the maxillary right central incisor and the rest of the subject's dentition, based on the subject's self-evaluation and analysis of digital photographs by the investigators.
4. The results showed a 35% improvement in tooth whitening (coefficient of reflection for white light), when compared with the tooth's original, natural color (see Table 5). No visible change in enamel gloss and reflection was observed.
5. After completion of treatment, review visits showed that the color change remained stable for a significant period of time. The results showed that one month after treatment, the whitening effect exceeded the original by 33% and four months after treatment, it still showed an approximately 15% improvement when compared with the original coefficient of reflection (Table 5).
6. At the four month review visit, no detrimental changes were observed in either the soft tissues or the enamel (no post-treatment caries was observed).

Conclusions:
The results showed that the use of a home based whitening system, using an edible acid visibly whitened the anterior teeth, with no discomfort to the user or damage to the soft tissues, and that the result remained effective for the four months of monitoring carried out in the study.

TABLE 5

Optical coefficient of reflection of enamel before and after treatment

|  | Normalized optical coefficient of reflection, a.u. |
|---|---|
| Before treatment | 1 |
| After 3 weeks of daily treatment | 1.34 |
| 1 months after treatment | 1.3 |
| 4 months after treatment | 1.15 |

In another embodiment of present invention, a tooth can be whitened in the following three sequential phases. During the first phase, an edible acid-based composition with pH between 0.5-5 is applied for 1 second to 60 minutes with temperature between 37° C. and 60° C. During the second phase, a bleaching compound comprising, for example, peroxide is applied via a gel, a strip, or a tray. During the third, optional, phase, a remineralization compound is applied. After the first phase, a new channel is created in the tooth structure for easy and quick penetration of the bleaching compound to extrinsic or intrinsic stain. As a result, the whitening effect of the acid-based compound is augmented by the bleaching compound, increasing overall bleaching effectiveness.

In yet another embodiment, the method and apparatus described above can be used for biologically active agent and/or stem cell delivery to hard tissue. In practicing this method, a porous layer is first created on bone, dentine, enamel, cementum, cartilage or nail tissue using the above-described process of controlled etching by an acid. The porous layer is then impregnated with, for example, a biologically active agent or a stem cell, which are subsequently dissolved in the hard tissue and the human body. This mechanism can be used in periodontal treatments for bone regeneration using stem cells released in bone tissue and cementum or dentine. In addition, this method and apparatus can be used to treat most common nail diseases and disorders, caused by fungal infections and bacteria, frequently characterized by weakening and discoloration of the nail plate. In practicing this method, a porous layer is first created on nail tissue using the above-described process. After this, a drug for treatment of infection or bacteria can be introduced into the porous layer and under such layer.

Tooth Coatings after Treatment with the Tooth Rejuvenation Compound

The effect of the tooth rejuvenation compound may leave the enamel surface with lowered hardness and wear resistance. This reduction is caused by partial de-mineralization of the enamel. Nevertheless, with the passage of time, these properties are restored because of the healing properties of saliva, which contains all of the necessary components for remineralization. The in-vitro and in-vivo tests conducted by inventors have shown that the action of the saliva results in restoration of the enamel hardness after application of the tooth rejuvenation compound within the period of several hours to one week depends on the initial depth of treatment. The gloss of the treated tooth is restored closely to that of original tooth without significantly reducing the whitening effect.

In addition, immediately after treatment with the rejuvenation compound, the enamel can be covered with a protective coating, permeable to the important compounds affecting the re-mineralization process. Such protective coating would be impermeable to the majority of organic molecules, which would otherwise pigment the enamel after beaching. The porous layer of enamel after treatment with the compound is better suited for bonding of coating material with tooth structure. The adhesion mechanism of such material may include etch-and-rinse, self-etch or glass-ionomer adhesion. An example of such a coating material is BISCOVER™ compound (BISCO, Inc.), which is a light cured composite. The effective adhesion of this coating material to a tooth treated with citric acid at a pH=1.5 with temperature 50° C. for 5 min was demonstrated. The result was a tooth surface, which was resistant to mechanical abrasion and acid attack. The optical, mechanical and chemical properties of the coating material can be improved by adding particles with special properties. The addition of sapphire, diamond, fianite, granite, topaz, amethyst, quartz, crystal, zircon, agate, spinel, and heavy flint glass particles increases scattering properties of the coating due to great differences between refractive indexes of particles and polymerized matrix. Scattering efficiency is directly proportional to the square of the difference between refractive indexes of the particles and of the matrix. Typical refractive index of the polymer matrix ranges from 1.4-1.55. Any particles from solid bio-compatible material with a refractive index higher than 1.6 are suitable for this effect. In addition, these particles can improve the wear resistance of the tooth. The size of these particles can vary between 10 nm-50000 nm. The particles can be arranged in the form of a sphere, a plate, or a fiber. In one embodiment, the fiber can be woven into a mesh. The mesh can be incorporated into the coating compound, applied to tooth after treatment with tooth rejuvenation compound, and then polymerized. This fiber can be made of quartz, glass, or crystal.

In another embodiment, the hard tissue surface is impregnated by a liquid silicon glass after etching. The above-described nano or micro particles can be added to the porous layer of the hard tissue or to the silicon glass. After drying of the liquid silicon glass in the porous layer, a modified layer of hard tissue with better mechanical, chemical and optical properties is formed. In addition, properties of this layer can be further improved by selective heating of this layer to the melting temperature of the silicon compound or of apatite, which is in the range of 1000-1200° C. Methods and apparatus for selective heating of this layer are described in detail below.

A special color center can be added to the coating material to provide a unique optical property to a tooth, e.g. ruby or alexandrite particles would produce a pink color. Gold, silver, or platinum particles could be added, as could organic dye molecules, which can be bleached at any time using UV light.

Nanoparticles (fullerenes or astrolenes), could be deposited immediately after cleaning. A solution of these particles penetrates the pores of the enamel and forms a thin film on its surface. Another coating of a material preventing the nanoparticles from diffusing into the environment surrounding the teeth is then deposited over the original thin film. The nanoparticles become locked in between the original thin film and the coating. Since it is known that the ability of nanoparticles to facilitate oxidation of the surrounding elements by generating singlet oxygen increases when the particles are exposed to light, the nanoparticles will oxidize the enamel of the tooth and bleach it more efficiently during the day when exposed to day light, and less efficiently at night. The effectiveness of such bleaching depends on the properties of the nanoparticles, their concentration as well as of the ability of the protective coating to diffuse oxygen, which should be sufficiently high.

Figure 15:
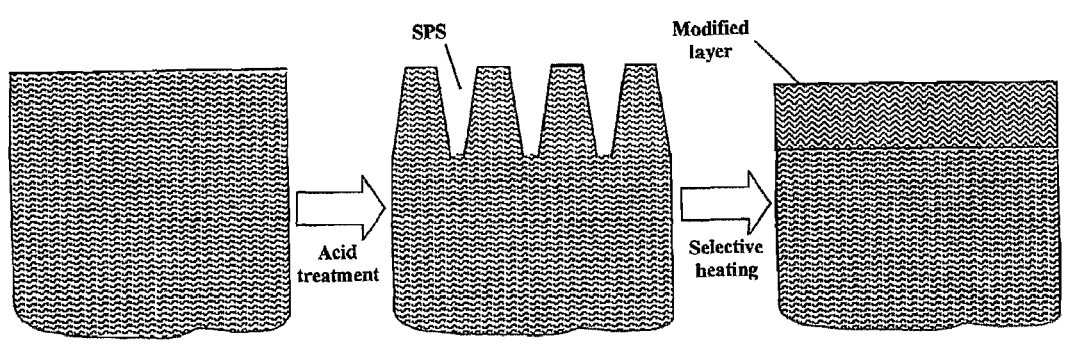
FIG. 15 is a schematic illustration of a process of treating an enamel surface by etching and selective heating of SPS.
Figure 16A:
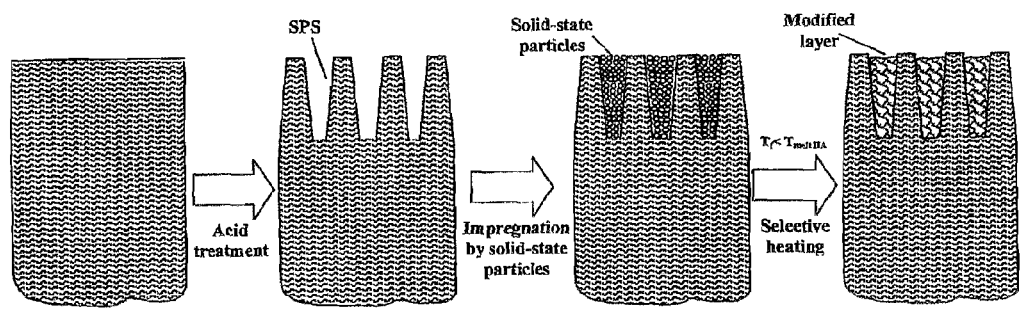
FIG. 16a is a schematic illustration of a process of treating an enamel surface with etching, impregnation by solid-state particles and selective heating to temperature $TF<T_{me}i_t$ of hard tissue.

Tooth Rejuvenation and Protection Due to Temperature Modification of the Tooth Surface A method and apparatus for professional tooth surface rejuvenation and whitening using edible acids was proposed and described in the above sections. This method can be further improved by additional selective heating the tooth surface. A method and apparatus for such heat treatment, which is described below, can be applied to etched hard tissue surface, carious tissue, or dentine and cementum tissue. In addition, the heat treatment can be used for treatment of gingival recession. Gingival recession is exposure of the tooth's root surface, caused by a shift in the position of the gingiva. Recession may be localized to one tooth or a group of teeth and may be visible or hidden. Caused by such factors as improper tooth brushing, gingival inflammation and aging, gingival recession promotes tooth's susceptibility to caries, sensitivity and undesirable esthetic appearance. The main requirement to hard tissue surface for such treatment is that superficial porous structure (SPS) must exist on the surface. To create SPS, it is preferable that an edible acid is used in the composition and apparatus described above, due to high safety profile for soft tissues and non-toxicity. Using edible acid is important for treating a large area of teeth, for example anterior teeth. However, in below-described methods other methods of control etching can be used. For example, phosphoric acid etching compound, which is developed for hard tissue etching before application of filling material or veneers, can be used as well. Three groups of such treatment are proposed in present invention: 1) a group of methods, based on the heating of the SPS with subsequent recrystallization, amorphization or ablation of at least some portion of the SPS layer (FIG. 15); 2) a group of methods based on the heating of the SPS layer impregnated with solid-state nano and micro particles (FIG. 16); 3) a group of methods, based upon the impregnation of the SPS by a preheated organic or mineral compound in the liquid phase (FIG. 17). After application of some or all of these methods, a superficial layer of hard tissue is formed. Such layer has enhanced optical properties, hardness and resistance to acid when compared with the original enamel or dentine. These methods can be used for tooth rejuvenation and protection, closure of carious lesions, treatment of hypersensitivity by sealing of dentine tubules, and treatment of periodontal disease. The three types of said treatment are described below.

Thermal Treatment of the Superficial Porous Layer of Hard Tissue

The previous method of hard tissue treatment using edible acid alters the hard tissue structure, by the formation of a layer of SPS with a depth varying from 0.5 to 100 µm, in a controlled manner. This change of hard tissue structure is accompanied by a deep cleaning of the surface of the hard tissue layer from staining, resulting into an improvement in tooth color. In addition, apatite crystals with micro-defects in the superficial layer of enamel are removed. Another effect of such treatment is removal of micro crystals with the lowest acid resistance, such as carbide apatite crystals. After such treatment, the surface layer of enamel is exposed to an intensive process of remineralization from saliva or other remineralizing rinses. However, the exposed layer of hard tissue can also be used for re-crystallization and the creation of a thin film of re-crystallized or amorphous apatite. This film has a higher acid resistance than natural hard tissue and additional light scattering properties, resulting in an improved aesthetic appearance of the tooth. It has been shown that the concentration of calcium (Ca), phosphorous (P) and fluorine (F) in the surface level of enamel is considerably higher than in that of the subsurface layer. The surface concentration of fluorapatite may be ten times more (10×) that of subsurface concentration of fluorapatite. However, the concentration of fluorapatite by weight is considerably less than that of hydroxyapatite. Under acid attack, the solubility of Ca ions in hydroxyapatite is considerably higher than the solubility of F ions. Therefore, the concentration of fluorapatite in modified enamel is increased considerably after acid attack. In the present invention, we propose laser post-treatment of the modified hard tissue surface layer as well as of the subsurface layer. Such treatment includes the selective heating of the modified surface layer as well of the subsurface layer to melting temperature, which ranges from 900° C. to around 1200° C. for enamel, and from 700° C. to around 900° C. for dentine. This is considerably lower than the evaporation temperature of these tissues, which is greater than 2000° C. After controlled cooling of the melted, modified hard tissue layer, a film is formed on the hard tissue surface in a crystallized or amorphous form. The film consists of crystallized or amorphous apatite, with a concentration of fluorapatite greater than that of the original enamel. This film improves the tooth's resistance to carious attack because: 1) an increased concentration of fluorapatite provides for a higher acid resistance against acids generated from biofilm or from foods; 2) the film has a higher density than regular enamel and is characterized by lack of defects and pores, which allow for penetration of bacteria and acids into subsurface enamel layers; 3) the film can function as a sintering surface for better post treatment remineralization from saliva or remineralizing rinses than for natural enamel. The film also has higher light scattering properties because the index of refraction for the re-crystallized layer is higher than the index of refraction of the subsurface layer of enamel due to a different chemical composition. Following re-crystallization, the surface layer is a glazed, mirror surface, with minimal scattering properties. However, the border between the re-crystallized layer and subsurface layer is irregular, with typical size of said irregularities equal to the size of the enamel prisms (5 μm). Such a border has high scattering properties. Light scattering from this border prevents the penetration of light into the subsurface tissue and reduces the portion of light scattered from subsurface layers of enamel and dentine in the general volume of light scattered from the tooth. Therefore, the cosmetic appearance of the tooth is determined more by the scattering of light from the border between the re-crystallized layer and the subsurface layer. The re-crystallized layer does not contain color centers, as these centers are removed during acid treatment. Therefore, the light reflected from the re-crystallized layer and from the subsurface layer is perceived as white. At the same time, scattering from the inner layers of enamel, which may be colored due to change in organic components due to aging, accumulation of color centers, penetrating tooth externally or internally (e.g. tetracycline), is suppressed. Such treatment can enhance the hardness of tooth the surface using proper post-cooling, which is described in detail below.

The proposed method includes two steps: 1) the formation of a layer of SPS on surface of hard tissue with a predetermined depth of 0.5-100 μm; 2) selective heating of the layer to a temperature ranging from 700-2000° C. and controlled post-cooling of the layer to form crystallized or amorphous film of apatite on the tooth surface. Pulsed heating of the layer can be with preheating pulse, which elevates temperature of the layer and under layer of tissue to meting point and is followed by heating pulse, which selectively melts the porous layer (melting pulse). The preheating pulse width $\tau_{pre}$ heat can be greater than or equal to the thermal relaxation time (TRT) of the porous layer (SPS). Melting pulsewidth $\tau_{me}$ it would be in the range of 0.1 TRT-10 TRT, preferably in the range between the TRT of the non-porous superficial layer and the us superficial layer. The TRT can be calculated using the formula:

$$TRT \approx \frac{d^2}{4-a}, \qquad (2)$$

where d is the thickness of the layer d≈0.5-100 μm, and α is the thermal diffusivity. For non-porous enamel $$a_{emml} \approx 0.004 \frac{cfn^2}{\sec}.$$

A porous layer with a porosity p has thermal diffusivity $a_{porms} \approx a_{emmel} \cdot (1-p)^{1/3}$. The porosity of the enamel after etching and drying can be in the range 0.1-0.7. Based on the formula (2), the TRT of the porous layer can be in the range as shown in Table 6.

TABLE 6

Thermal relaxation time of the enamel layer in μs.

| Enamel layer thickness, microns | Porosity | | | | |
|---|---|---|---|---|---|
| | 0 | 0.1 | 0.3 | 0.5 | 0.7 |
| 0.5 | 0.16 | 0.16 | 0.17 | 0.20 | 0.23 |
| 25 | 390.63 | 404.59 | 429.94 | 492.16 | 583.52 |
| 50 | 1531.00 | 1586.00 | 1686.00 | 1929.00 | 2288.00 |
| 75 | 3422.00 | 3545.00 | 3767.00 | 4312.00 | 5113.00 |
| 100 | 6064.00 | 6281.00 | 6674.00 | 7640.00 | 9058.00 |

The melting pulse width can be in a range from 16 ns to 90 ms. The preheating pulsewidth can be in the range from 160 ns to 90 ms. Cooling of the melted enamel or dentine layer is important for the formation of a new layer of hard tissue to provide better optical, mechanical and chemical properties. Rapid post-cooling leads to the formation of a mostly amorphous glass-like structure. Slow post-cooling leads to the formation of mostly a fine or coarse-crystalline structure. The crystalline structure may be more preferable for thick modified layer. An amorphous structure may be more preferable for a thin modified layer. For some applications, the modified layer can be formed with a deep crystalline structure and a thin superficial amorphous layer. Cooling can be passive or active. The tooth can be cooled by allowing heat to dissipate into the tooth structure (passive cooling) or the tooth can be cooled from the heated surface with a cooling gas or liquid (active cooling). For example, a water layer with a thickness ranging from 10 μm to 5 mm can be applied to the surface of the treated tooth with or after the melting pulse. In this case, heat is removed by thermoconduction to the water layer, leading to its heating and vaporization. Post-cooling may be beneficial to decrease the residual amount of heat remaining on the tooth after treatment. To extend the post-cooling time, a long post-heating pulse can be applied to the treated layer of hard tissue. The post-heating pulse duration can be from TRT of melted layer to 1 sec. Controlled post-cooling can prevent the formation of droplets on the surface during solidification. The amount of heating energy required for this treatment can be calculated using the formula:

$$F = d \cdot p \cdot (1-p) \cdot (Q + c \cdot \Delta T), \quad (3)$$

, where p is the enamel density, c is the enamel-specific heat capacity, Q is the enamel-specific heat of melting, $\Delta T = T_{melt} - 37$, $T_{melt}$ is the temperature to melt the hard tissue. The minimum fluence of heating energy for melting as a function of thickness of the porous layer and porosity is shown in Table 7.

TABLE 7

Fluence of heating energy for melting the porous layer of enamel in J/cm²

| Enamel layer thickness, microns | Porosity | | | | |
|---|---|---|---|---|---|
| | 0 | 0.1 | 0.3 | 0.5 | 0.7 |
| 0.5 | 0.19 | 0.17 | 0.13 | 0.09 | 0.06 |
| 25 | 9.46 | 8.51 | 6.62 | 4.73 | 2.84 |
| 50 | 18.73 | 16.85 | 13.11 | 9.36 | 5.62 |
| 75 | 28.00 | 25.20 | 19.60 | 14.00 | 8.40 |
| 100 | 37.27 | 33.54 | 26.09 | 18.63 | 11.18 |

It follows from the above table, that the range of minimum heating fluence for the described method is $F_{melt} = 0.06 - 37$ J/cm². The fluence for this treatment is G times higher than $F_{melt}$, where G is the inverse efficiency of absorption of the heating energy in the treated layer. For dentine treatment, the fluence is 2-4 times lower than that for enamel. Table 7 shows that porous tissue has a melting fluence 1.1-3.1 times lower than that of intact tissue. This property can be used for selective treatment of tissue processed with acid in such a manner as to not affect the untreated tissue. To do this, the fluence must be selected from the range of $G \cdot F_{melt} < F < G \cdot (1.1-3.1) \cdot F_{melt}$.

The heating of the SPS layer in the present invention can be achieved using several energy sources, including, but not limited to, electromagnetic energy sources, such as a laser, microwave generated sources, electrical current sources, such as direct current, low or radio frequency current sources, or acoustic sources.

Figure 10:
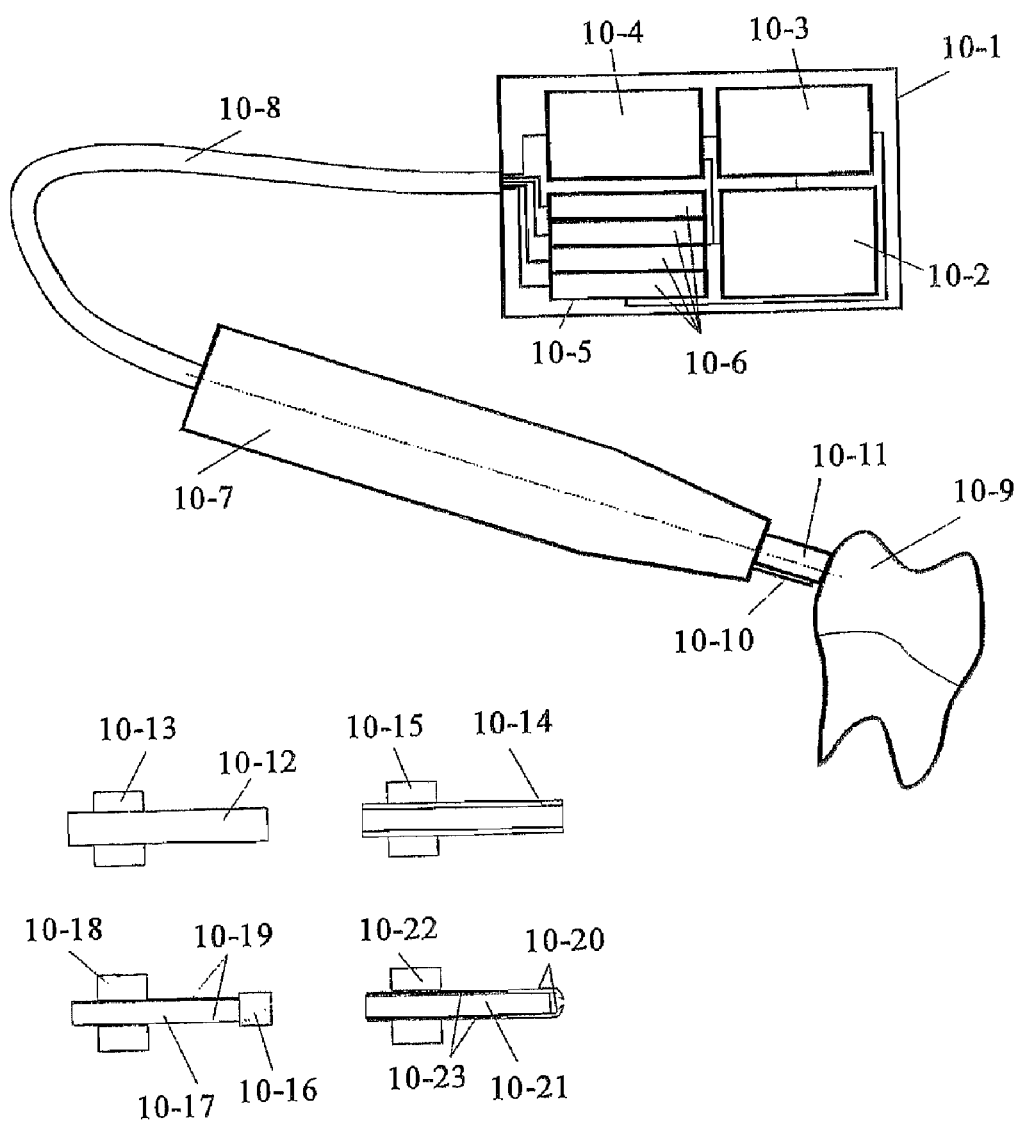
FIG. 10 is a schematic illustration of one of the embodiments of a device for selective heating of hard tissue surface with a hand piece.

One embodiment of present invention is shown in FIG. 10. The device comprises of a power supply 10-2, a control unit 10-3, a cooling unit 10-4 and an energy source unit 10-5. Unit 10-5, in turn, may comprise of one or more energy modules 10-6, each generating its own energy type (e.g. laser radiation, microwave, acoustic wave, high-frequency current, etc.). The main unit 10-1 is connected to a handpiece 10-7 by way of a flexible tube 10-8, which, in turn, may contain flexible tubes for the transmission of cooling liquid from 104 to the tooth surface 10-9 via a jet 10-10. In addition, the flexible tube 10-8 may contain optical fibers or hollow waveguide for transmission of laser energy and/or hollow waveguide for transmission of microwaves to 10-9 via the tip 10-11, and/or electric wires for supply of electrodes, and/or the acoustic transducer situated in 10-11. The tip 10-11 transmits to the tooth 10-9 one or several energy types. For transmission of laser energy, the tip 10-11 may be an optical fiber 10-12, fixated in holder 10-13. For transmission of microwaves, the tip 10-11 may be a hollow tube 10-14, fixed in holder 10-15. For creation of an acoustic wave on the surface 10-9, the tip 10-11 may be an acoustic transducer 10-16, fixed in a rod 10-17, which, in turn, is fixed in a holder 10-18. Energy is delivered to the acoustic transducer is done via wires 10-19. Electrodes 10-20 may be used for the creation of a high-frequency discharge on the surface 10-9. The distance between exposed electrode tips 10-20 may be between 0.1 mm and 1 mm. The electrodes 10-20 are situated in a rod 10-21. The rod is fixed in a holder 10-22. Energy is delivered to the electrodes 10-20 via wires 10-23. Holders 10-13, 10-15, 10-18 and 10-22 attach these structures 10-11 to a tip 10-7.

In addition, a sensor 10-10 for feedback-controlled treatment can be incorporated into the tip. The sensor can be used for differentiation of the porous layer from intact hard tissue or soft tissue, measurement of the temperature of the layer's, measure melting point, and measurement of contact with the tissue. This sensor can be mechanical, electrical, optical or acoustic. For example, it can be an IR sensor for measuring the temperature of the surface, as shown. The signal from the sensor is sent to control electronics 10-3 and is used to control the level and temporal profile of the heating energy. The shape of the tip 10-11 can be round, with a diameter of 0.05-3 mm, or rectangular. Two different types of energy can be combined for heating. For example, pre-heating and post-heating pulses can be microwave, electrical or acoustical pulses, while the melting a laser beam with a diameter once it reaches the surface, of 0.01-0.5 mm can be controlled by a micro scanner to produce uniform or predetermined non-uniform patterns on the tooth surface. This device can be used for treatment of all teeth. The treatment area can be controlled by the operator and moved from site to site by the hand of the operator. This device can be used for the selective treatment of fissures, dentine periodontal area, sharp edges of a tooth, and carious lesions. The device can also be used for preparation of tooth surface prior to application of filling or crown material and veneers. In this case, special surface profile can be created on the tooth's surface for better bonding. The modified layer of the tooth's surface can provide additional protection against recurrent caries, for periodontal decease prevention and healing, hypersensitivity treatment.

Figure 11:
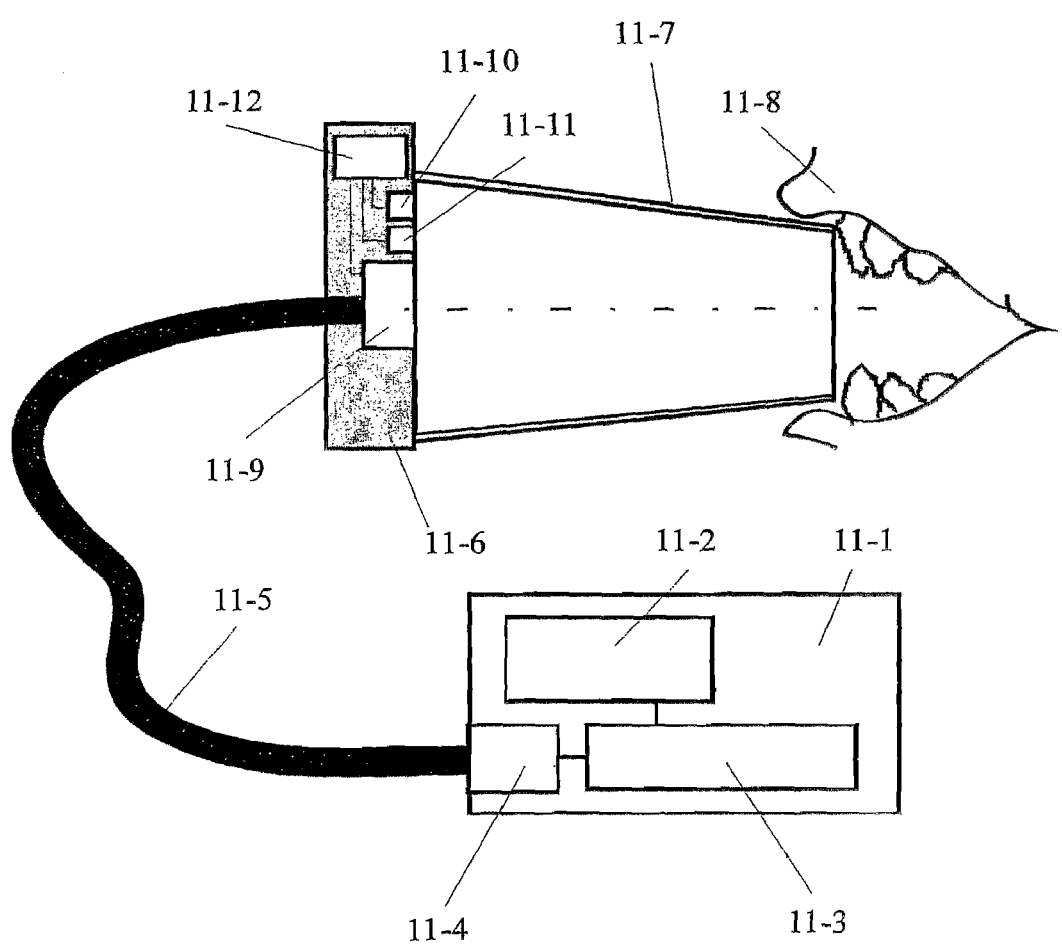
FIG. 11 is a schematic illustration of one of the embodiments of a device for selective heating of hard tissue surface with a mouthpiece.

In another embodiment, the anterior teeth can be heated using an automatically scanning laser beam, as shown in FIG. 11. This device may contain a main unit 11-1 with a power supply 11-2, a laser with optics 11-3 and an optical coupler 11-4 into the fiber 11-5. Laser energy through the fiber 11-5 is delivered into a mouthpiece 11-6. The mouthpiece comprises of a body 11-7, held in the mouth 11-8 of the patient, an optical two or three-dimensional scanner with focusing optics 11-9, an optical video camera 11-10 and an optional thermo camera 11-11. Signals from the cameras are transferred to control electronics 11-12, which controls the scanning mode of operation of the scanner 11-9. The image from the cameras 11-10 and 11-11 can be presented on a monitor. The operator can use the image on the monitor for determining treatment areas, for programming the scanner, and for real time observation of treatment.

Laser sources for practice of this invention can be selected from those lasers with energy and pulse width described above, and wavelengths, which are primarily absorbed in treated layer of hard tissue. In preferable embodiment, laser light penetration into the hard tissue must be close to or lower than the thickness of the treated layer, which for this invention is in the range of 0.5-100 μm. The depth of penetration in the tissue is expressed by the formula, $h = 1/(\mu_{abs}(\lambda) + \mu_{scatt}(\lambda))$ where $\mu_{abs}(\lambda)$ and $\mu_{scatt}(\lambda)$ are the coefficient of absorption and the coefficient of scattering of the tissue as a function of the wavelength λ, respectively. For $h = (0.5-100)$ μm, $(\mu_{abs}(\lambda) + \mu_{scatt}(\lambda))$ is approximately $(20000-100)$ cm⁻¹. Such strong absorption of enamel is found in the wavelength range $\lambda$=1.85-11 µm, preferably $\lambda$=2.7-3 µm and $\lambda$=8.7-11 µm, and most preferably $\lambda$=9.1-9.7 µm. Strong absorption and scattering of enamel is for the wavelength $\lambda$=0.15-0.4 µm, preferably $\lambda$<0.2 µm. In porous enamel or dentine in this range of wavelengths, the coefficient of absorption can be several times higher than in non-porous tissue due to the optical resonance (Mi resonance) on small particles in a porous structure. For the IR range of wavelengths Er, $CO_2$, CO, quantum cascade diode lasers, a fiber laser with diode laser pumping and optical parametric oscillators (OPO) can be used. For the UV range, excimer laser, solid-state lasers and a diode laser with a non-linear converter can be used. For example, a diode pumped Nd laser can be used with a 3, 4 or 5 wave non-linear converter. The laser can be built either into the main unit or into the handpiece. In another embodiment, one part of the laser system can be built into the main unit and another into the handpiece. For example, the Nd laser can be built into the main unit and laser energy can be delivered to the handpiece through an optical fiber. The non-linear converter can be built into the handpiece for direct delivery of UV light to the treatment zone. The lasers are described in greater detail below.

Heating of the SPS Impregnated by Solid-State Nano and Micro Particles

In another embodiment of present invention, the superficial porous structure (SPS) on hard tissue is filled with nano or micro particles and selectively heated to a temperature at which at least one component of the impregnated porous layers is melted to create a ceramic layer on the hard tissue surface after cooling. This method includes three steps as described below and shown in (FIG. 16):

1) Using the tooth rejuvenation compound, based on an edible acid or other acid in the controlled manner described above, a porous layer (superficial porous structure (SPS)) of hard tissue with a thickness of 0.5-100 µm is formed on the tooth surface. A carious lesion or dentine surface with open dentinal tubules can also be considered as a porous surface and treated in this manner.

2) Solid particles, with size smaller than the size of the pores, are impregnated into the porous structure using one of several conventional methods, such as painting of the suspension of the particle on the surface, application under pressure, etc.

3) The porous layer with the particles is selectively heated to a temperature sufficient to create strong bonding between the atoms of the particles and the atoms of the porous structure of hard tissue using the heating methods and apparatuses described above.

The size of the pores in the hard tissues prior to etching, and after etching is within the range of 10 nm to 5000 nm. The particle size must also be within this range, preferably within 5 to 4000 nm. After heating of the porous layer impregnated with solid particles, at least one of the components is melted and, after solidification of the weak layer of SPS, is replaced by a dense ceramic-like layer coating. The optical mechanical and chemical properties of this new layer can be optimized as necessary by selection of the type of the particles to be used. For example, by using particles with hardness greater than that of enamel it is possible to improve the wear properties of a tooth. Similarly, by using particles with a refractive index very different from apatite, scattering reflection and therefore, strong permanent whitening effect can be achieved. It is possible to create a ceramic with an acid resistance much greater than that of enamel or dentine. The ceramic-like layer is strongly bonded to the tooth because it is formed from to the tooth's porous layer, which is part of tooth's structure. This method can provide an improvement to the appearance of a tooth, better than is currently provided using veneers, with the significantly added benefit of not removing hard tissue or needing local anesthesia.

During the heating of layer of the SPS impregnated with particles, at least one of the components of this layer must be melted and liquified to a viscosity low enough to fill the pores. The dynamic viscosity of this heated component must be below $\eta F$=10 Pa-s, preferably in the range of 1 to 0.0001 Pa-s. The temperature, when the solid state after melting exceeds this viscosity, is defined as the fluidity temperature TF. For crystals, $T_F$ is almost equal to the melting temperature $TF \sim T_{me}it$. For glass, $T_F$ is higher than temperature required to melt glass $T_{me}i_t$, $T_F = T_{me}i_t + (100 \div 500)$. The $T_F$ for glass-like composition can be calculated by the following formula:

$$T_F \approx E/[R - \ln(\eta_F/\eta_0)], \quad (4a)$$

where E is activation energy, $\eta o$ is pre-exponential factor, and R=8.3 J/mol-K. The $T_F$ can be also calculated by the following formula:

$$T_F << \{[(r_t - T_2)ZT_1 - T_2] - \sqrt{h}x(\eta_F IVx) \cdot \ln(v_2/\eta_1)] + 1/T_1\}^{-1}, \quad (4b)$$

where $Ti_{,2}$ is a temperature, when viscosity is $\eta_{1,2}$ respectively, $T,i_{,2}$ can be transformation temperature ($\eta = 10^{1L3}$ Pa-s), softening temperature ($\eta = 10^{6.6}$ Pa-s) or melting temperature ($\eta$=10 Pa-s).

The present invention proposes the use of three types of particles.

1) Particles with a fluidity temperature $T_F$, lower than the temperature of melting of hard tissue (FIG. 16a), which is in the range of 1000-1200° C. for enamel and in the range of 700-900° C. for dentine. Therefore, $T_F$<1000° C. for enamel and Tp<700° C. for dentine. In this case, only the particles will melt and the SPS will not change during heating. The melted particles will fill the pores of the hard tissue and fuse with it, bonding to the tissue. One advantage of this method is the low energy needed for heating, which results in a low cost of device. A lower temperature is also better for the tissues of the pulp and allows for very good bonding to the hard tissues. In the preferred embodiment, the coefficient of thermal linear expansion (CTLE) of the particles must be above that of apatite (CTLE=9-$10^{-5}$) and below that of hard tissue. This would improve the strength of the bond during cooling and compress the composite/ceramic layer, avoiding micro cracks. The particles to practice this method can be organic, such as polymethylmethacrylate (PMMA), polycarbide, epoxy, etc. They could also be made of glasses, from the group of fluoride, phosphate, lanthanum or silica glasses. The fluoride glasses with a composition, such as $ZrF_4$—$BaF_2$—$LaF_3$—$AlF_3$—NaF, have a $T_F$=490-800° C. Silica glasses with a compositions, such as $Li_2O$—$SiO_2$ or $Na_2O$—$SiO_2$, have a $T_F$=440-500° C. or $T_F$=360-410° C., correspondingly. Also crystals, such as $Ca(NO_3)_2$ ($T_{me}it$=560° C.), $Ca(OH)_2$ ($T_{me}i_t$=500° C.), $BaO_2$ ($T_{me}i_{t-}$=450° C.), $CdCl_2$ ($T_{me}i_t$=570° C.) and others can be used to practice this invention.

Figure 16B:
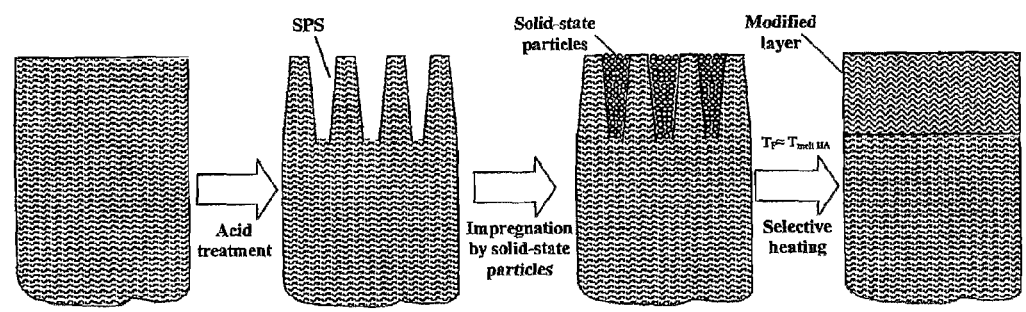
FIG. 16b is a schematic illustration of a process of treating an enamel surface by etching, impregnation by solid-state particles and selective heating to temperature $T-p-Tmei_t$ of hard tissue.

2) Particles with a fluidity temperature $T_F$ in the range of the melting temperature of enamel 1000° C.<$T_F$<1200° C. or dentine 700° C.<$T_F$<900° C. (FIG. 16b). In this case, both the particles and apatite are heated to the melting temperature, and are allowed to cool, creating an amorphous or polycrystal-like structure (composite/ceramic structure), depending on the heating and cooling regime used (described in detail above). The advantage of this method is the uniformity of the new composite/ceramic structure produced, and its high acid resistance. In the preferable embodiment, the CTLE of the new composite/ceramic layer must be lower than that of apatite (CTLE=9-$10^{-5}$), thereby compressing the composite/ceramic layer and avoiding micro cracks during cooling. For this method, the particles used must be mineral, non-organic particles, such as glass or crystal, or a mixture of both. For example, the glass may have a composition such as $Na_2O$—$Al_2O_3$—$SiO_2$, and the crystal, a composition such as $Ca(PO_3)$ ($T_{melt}=984°$ C.) or $CdF_2$ ($T_{melt}=1072°$ C.).

Figure 16C:
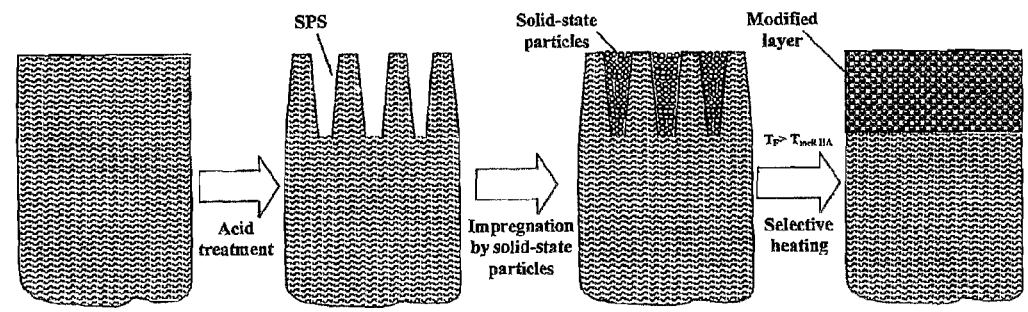
FIG. 16c is a schematic illustration of a process of treating an enamel surface by etching, impregnation by solid-state particles and selective heating to temperature $TF>Tmei_t$ of hard tissue.

3) Particles with a fluidity temperature TF in the range higher than the melting temperature of enamel ($T_F>1200°$ C.) or dentine ($T_F>700°$ C.) (FIG. 16c). In this case, after heating, the porous layer is impregnated with particles heated to a temperature higher than their temperature of fluidity TF. The new structure is similar to the one described above. However, if the temperature is higher than the melting temperature of hard tissue but below the melting temperature of the particles, the composite/ceramic layer would be composed of solid particles bonded to the amorphous or crystallized apatite. One advantage of this method is the very high hardness of the new layer. In the preferable embodiment, the CTLE of the new composite/ceramic layer must be lower than that of apatite, compressing it, thereby avoiding micro cracks formation would be avoided during cooling. Lithium glass $Li_2O$—$B_2O_3$, for example $20Li_2O$—$SOB_2O_3$, with very low CTLE can be used to practice this invention. In this case, the particles to practice this method must be mineral, non-organic particles, such as glass or crystal and/or their mixture. Examples of appropriate glasses are quartz glass and sital glass. Glass with compositions, such as ($Na_2O$, CaO, $SiO_2$), ($Na_2O$, PbO, $SiO_2$), ($Al_2O_3$, $Na_2O$, $SiO_2$) ($Na_2O$, $B_2O_3$, $SiO_2$) can also be used. Examples of crystal are crystal quartz ($T_{melt}=1700°$ C.), diamond ($T_{melt}=3900°$ C.), sapphire $Al_2O_3$ ($T_{melt}=2046°$ C.), $AlPO_4$ ($T_{melt}=2000°$ C.), or $CaTiO_3$ ($T_{melt}=1960°$ C.), hydroxyapatite $Ca_{10}(PO_4MOH)_2$ ($T_{melt}=1614°$ C.), fluorapatite $Ca_{10}(PO_4)_6F_2$ ($T_{melt}=1612$-$1680°$ C.). These crystals can also be chosen from the group of gem crystals, including, but not limited to, topaz, amethyst, zircon, agate, granite, spinel, fianite, tanzanite, and tourmaline. The particles can be made from high temperature ceramic and polycrystalline. The properties of some preferable particles used to practice the present invention are shown in Table 8. The TF was calculated using formula (4).

Table 8. Material of the Particles and their Property

TABLE 8

Material of the particles and their properties.

| Material | | Temperature of melting $T_{melt}$ or fluidity $T_F$, C. ° deg. |
|---|---|---|
| Name | Composition, % | |
| Diamond | C | 3700-4000 |
| Sapphire | $Al_2O_3$ | 2040 |
| Hydroxyapatite | $Ca_{10}(PO_4)_6(OH)_2$ | 1614 |
| Quartz crystal | $SiO_2$ | 1610-1720 |
| Sheelite | $CaWO_4$ | 1580 |
| Fluorite | $CaF_2$ | 1418 |
| Glass | $50BaO$-$50SiO_2$ | 1670 |
| | $50CaO$-$50SiO_2$ | 1600 |
| | $28.4MnO$-$29Al_2O_3$-$38SiO_2$ | 1600 |
| | $25MgO$-$25CaO$-$50SiO_2$ | 1500 |
| | $50SrO$-$SiO_2$ | 1460 |
| | $50Li_2O$-$50SiO_2$ | 1350 |
| | $50PbO$-$50SiO_2$ | 1100 |
| | $30Na_2O$-$10CuO$-$60SiO_2$ | 1100 |
| | $19.7Na_2O$-$10.6Al_2O_3$-$69.7SiO_2$ | 1050 |
| | $30Li_2O$-$18B_2O_5$-$52SiO_2$ | 940 |
| | $50Na_2O$-$50SiO_2$ | 900 |
| | $9Na_2O$-$38.7PbO$-$52.3SiO_2$ | 850 |
| | $25.3Na_2O$-$53.6GeO_2$-$21.1SiO_2$ | 650 |
| | $50K_2O$-$25TiO_2$-$25SiO_2$ | 600 |

Dental ceramic composition (porcelain) can be used as particles to fill porous layer of the tooth. Low fusing dental porcelain frit, such as $68.6SiO_2$-$8.4Al_2O_3$-$1.84CaO$-$7.82K_2O$-$4.66Na_2O$-$0.1TiO_2$-$7.87B_2O_3$-$0.07Fe_2O_3$-$0.01Li_2O$, with fusion temperature 850/1050° C. can be used as the first or the second type of particles. Medium fusing dental porcelain frit, such as $64.7SiO_2$-$13.9Al_2O_3$-$1.78CaO$-$7.53K_2O$-$4.75Na_2O$-$0.05TiO_2$-$7.28B_2O_3$-$0.07Fe_2O_3$-$0.0ILi_2O$, with fusion temperature 1050/1200° C. can be used as the second or the third type of particles.' High fusing dental porcelain frit, such as $62.7SiO_2$-$17.1Al_2O_3$-$1.72CaO$-$6.94K_2O$-$4.245Na_2O$-$0.02TiO_2$-$6.92B_2O_3$-$0.07Fe_2O3$-$0.01Li_2O$, with fusion temperature 1200/1450° C. can be used as the first or the third type of particles.

Using gem crystals, the coating can create an entirely new appearance of the tooth, by controlling its color. For example, by using ruby crystal particles, the tooth would acquire a pink tone, with tanzanite or natural sapphire, a blue tone, while tourmaline would create a green tone. Diamond particles provide maximum scattering effect due to very high refractive index (n=2.5). Color of the coating can be adjusted by addition of small amounts of chromophore, such as Co or NaI, colloidal metal, such as Au, Ag, Pb, As, Sb, or Bi, semiconductor quantum dots, such as CdS, $CdSe_5$ CdTe, or ZnS. Photosensitive glasses, containing Au, Ag, Cu or other ions, can be used to provide color or darkness of the tooth, which is changes, depending upon light expose or temperature. In addition to dielectric particles, metal particles, including, but not limited to, Au, Pt, Ag, Cu or Ce could also be used. These particles would provide a unique cosmetic appearance and good wear and acid resistance to the tooth. These particles can be used for increasing selective absorption of the porous layer by laser heating or by changing of electrical properties of the layer by selective electrical heating. For example, adding Ce ions can increase absorption of the layer in the UV wavelength range. Selective heating of the porous layer, impregnated with nano or micro particles, can be achieved with light, microwave, electrical current and acoustic energy using the methods and apparatuses described in previous sections. Energy can be selectively deposited not only in the porous hard tissue layer, but also within the particles, which can be selectively heated to their melting point. This can for example be achieved using a laser. The wavelength of the laser must be selected from within the range where the ratio of the coefficient of absorption of the particles to the coefficient of absorption of the hard tissue is more than 2, preferably more than 10. The pulse width can be shorter than the TRT of the particles or their clusters, while the fluence is determined by equation (3). Due to optical or plasma resonances, it is important that the coefficient of absorption of the nano and micro particles can be significantly higher than that of the bulk material. The laser fluence can then be decreased, providing better safety of treatment and a lower cost of device. Lasers in the visible and near infrared range can be used for selective heating of the particles.

Figure 13:
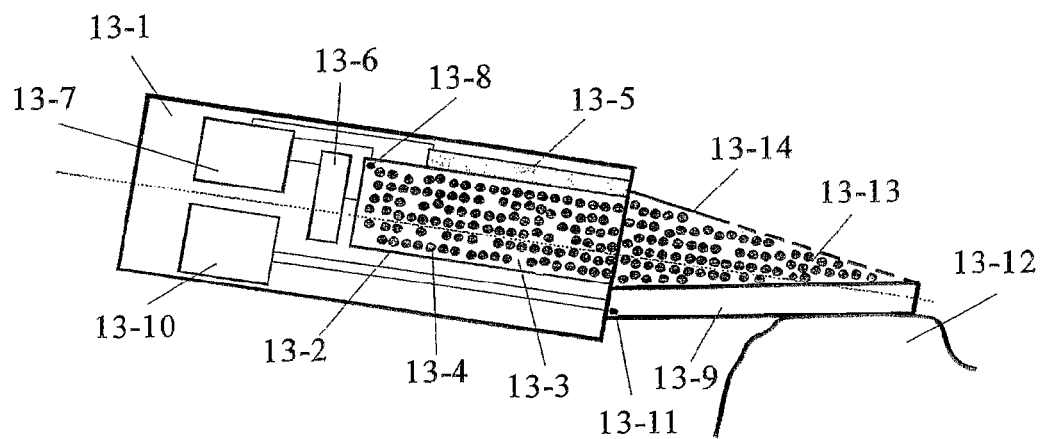
FIG. 13 is a schematic illustration of another embodiment of a device for selective heating of hard tissue surface with a hand piece.

FIG. 13 shows yet another embodiment of the device, comprising of a probe 13-1, reservoir with the mixture 13-2 (e.g. in the form of gel) of a water-based acid solution 13-3 (e.g. using citric acid) and solid-state particles 13-4 (e.g. sapphire, diamond, etc.), a heater 13-5 for the mixture 13-2, a device to expel the mixture 13-6, a power supply and control unit 13-7, and a temperature sensor 13-8 of the mixture 13-2. The device also contains a heater 13-9 connected to the power supply and control unit 13-10. The temperature of the heater 13-5 is controlled by a sensor 13-11. A heater 13-5 is used for heating the mixture 13-2. Another heater 13-9 is used for melting of the modified hard tissue layer 13-2 by the tooth rejuvenation compound 13-3, which contains solid-state particles 13-4. The mixture 13-2 is delivered to the enamel upon contact of one side 13-13 of the tip 13-14 with the enamel. Heating of the modified enamel layer to the melting temperature occurs on contact of the heater 13-9 with the layer.

Figure 14:
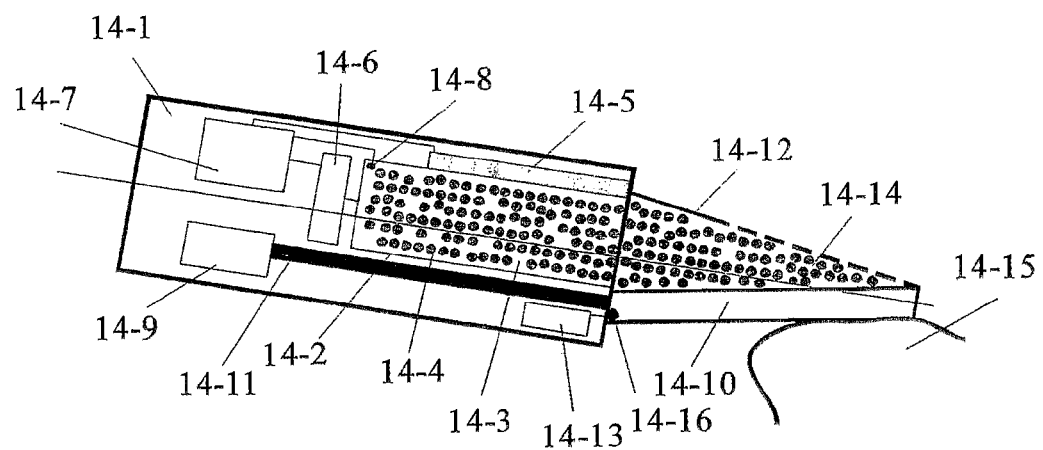
FIG. 14 is a schematic illustration of yet another embodiment of a device for selective heating of hard tissue surface with a hand piece.

FIG. 14 shows one embodiment of the device, comprising of a probe 14-1, a reservoir with the mixture 14-2 (e.g. in the form of a gel) of the water-based acid solution 14-3 (e.g. using citric acid) and solid-state particles 14-4 (e.g. sapphire, diamond, etc.), a heater 14-5 for the mixture 14-2, a device for expelling the mixture 14-6, a power supply and control unit 14-7, and a temperature sensor 14-8 of the mixture 14-2. The device also contains a laser energy source 14-9, connected to a scanner 14-10 by an optical pathway 14-11 (e.g. optical fiber). The scanner is situated in the tip 14-12 and connected to the power supply and control unit 14-13. The mixture 14-2 is delivered to the enamel upon contact of one side 13-14 of the tip 13-12 with the enamel 14-15. The laser radiation transforms the enamel layer, modified by the acid, upon contact of the scanner 14-10 with said layer. The device also contains a contact sensor 14-16 connected to the power supply and control unit 14-13.

Example 3

Thermal Treatment of Etched Enamel Impregnated by Sapphire Particles

The authors produced a durable, white colored coating on the enamel surface in an in-vitro experiment as described below. The experiment was conducted on freshly extracted teeth from subjects in the 25-40 age group. The teeth were extracted for periodontal reasons. All specimens had healthy, intact enamel. Prior to the experiment, the specimen were stored for no longer than two weeks in a physiological solution, in a dark place at a temperature of approximately +4° C.

One half of the crown of the tooth was coated with varnish. The specimen was men placed in water-based solution of edible citric acid with a pH=1.5 at a temperature of approximately +50° C. The tooth was exposed to the acid for a period of approximately 10 minutes, which was sufficient for the formation of a porous layer of enamel, approximately 50 μm in thickness on unprotected side of the specimen. Following exposure to the acid, the side of the tooth with the varnish had the coating removed, the tooth was washed with distilled water, and the part exposed to the acid was processed using a $CO_2$ laser.

Prior to laser processing, a 30-50 nm thick layer of sapphire particles with a diameter of 0.1 nm was applied onto the part of the enamel previously exposed to acid. A pulsed $CO_2$ laser with a wavelength of 10.6 nm, a pulse length of 100 μs, a frequency of 250 KHz and a beam diameter on the tooth surface of 50 μm was used. Average power of the laser was varied in the range 0.5-1 W. The laser beam was moved across tooth surface to covering large area using a 2D scanner.

Subsequent analysis of the images of the treated zones showed that the use of sapphire particles and $CO_2$ laser on chemically modified enamel produced a layer with very high scattering properties, negligible absorption of visible light, and with very good specular reflection properties. The optical properties of this layer did not change after three days of storage in water. This layer almost completely blocked scattering light from the internal structures of the tooth. As a result, the appearance of the tooth is was independent of any discoloration due to aging and the use of drugs. This layer also forms an excellent bond with the underlying intact tissue, and provides the tooth surface with a significantly harder surface than that prior to treatment. The hardness is significantly higher than that of alumina silica glass, which, in turn, is more than 1.2 times harder than intact enamel. The newly produced surface could scratch glass whereas enamel cannot. This property of the altered enamel surface is in all probability due to the presence of sapphire particles in the newly formed layer.

Thermocycling test was performed after described treatment The tooth was placed into two alternate water baths, one at +25° C. and the other at +90° C., for a period of 2 seconds into each bath, for a total immersion of 100 cycles. The hardness of the treated and untreated sides was assessed, before and after thermocycling, using a dental probe. The strength of the adhesion of the newly formed layer with sapphire particles to the underlying enamel was also assessed using the tip of the dental probe in an attempt to dislodge the newly formed layer at the border. The experiment showed that thermocycling led to no change in the hardness or degree of adhesion of the newly formed, white layer to the underlying enamel. Optical microscopy of a cross section of treated enamel, perpendicular to the surface showed that there was no sharp, defined boundary between the modified and unmodified enamel, which explained the high stability of the modified enamel layer after thermocycling.

Impregnation of the SPS by the Preheated Compound in the Liquid Phase

In another embodiment of the invention, the superficial porous structure (SPS) on the hard tissue is filled by a compound preheated to liquid phase. At body temperature, the compound is in the solid-state phase. The melted compound impregnates SPS of hard tissue and creates a ceramic layer on the hard tissue after cooling. This method takes up to three steps (the second step is optional) (FIG. 17):

1) Using the tooth rejuvenation compound based on an edible acid or other acid in the controlled manner described above, a porous layer of hard tissue with thickness of 0.5-100 μm is formed on the tooth surface. The surface could also be carious lesion or dentine with open dentine tubules.

2) (Optional) Solid-state nano or micro particles, with a size smaller than the size of the pores (10-5000 nm), are impregnated into the porous structure using one of several conventional methods, such as painting of suspension of the particles, application under pressure, etc.

Figure 17A:
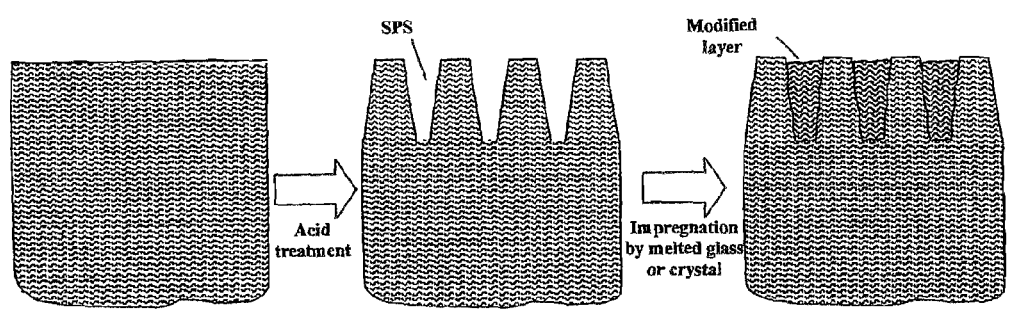
FIG. 17a is a schematic illustration of a process of treating an enamel surface by etching and impregnation by melted glass or crystals.
Figure 17B:
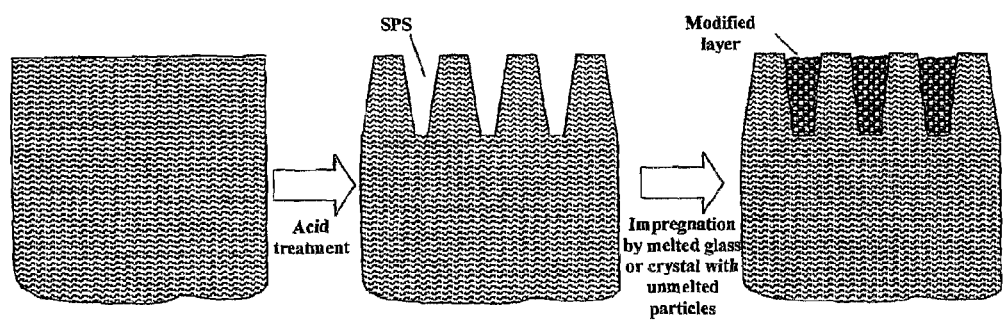
FIG. 17b is a schematic illustration of a process of treating an enamel surface by etching and impregnation by melted glass or crystals mixed with solid particles.

3) The solid-state particles or a fibrous thin film of material are heated to the fluidity point $T_F$ in close proximity to the tooth surface and are impregnated into the porous structure using external pressure or capillary power. The cooling phase begins after impregnation of the porous structure by the hot liquified material. During the cooling phase, if the $T_F > T_{melt}$ of enamel (800-1200° C.) porous enamel can be partly or completely melted and formed into a ceramic layer (FIG. 17a). If the $T_F > T_{melt}$, after cooling, a heterogeneous structure of the SPS filled with the solidified material is formed. If the second step is taken, the properties of the new layer can be optimized by changing the type of particles in this step. For example, if these particles have a melting temperature higher than $T_F$, then after cooling they are not changed and can provide the new layer with high hardness and good light scattering properties. Sapphire, ruby and other group of gem crystals, ceramic, or quartz crystal may be used. The particles may also be mixed with a low melting glass or crystal prior to delivery to the tooth surface (FIG. 17b).

The liquified material can be delivered to the SPS under pressure for better impregnation. Alternatively, the liquified material can impregnate into the SPS under the action of capillary pressure. Penetration coefficient of the liquified material must be maximized by selection of material with high surface tension, low contact angle (good wetting) and heating to the temperature higher than fluidity temperature For superior mechanical properties of the new layer, during compression of this layer, the compressive forces must be applied in a direction perpendicular to the tooth surface during the cooling phase. This compression can occur if the solid phase of the material has a lower density than the liquid phase. For example, a glass from the group of sital, $CrO_2$, CdS can be used. The cooling phase can be passive, by conduction into the deeper tissues or enhanced by surface cooling using a gas or liquid flow.

In another embodiment, a thin film of glass can be applied to the tooth surface. The thickness of such film can range between 5-100 μm. The film can be pre-cut to match contour of the tooth. Such film is soft and can be attached to the tooth surface by slight pressure. After that, the film can be heated to temperature $T_F$ as are described above.

Figure 12:
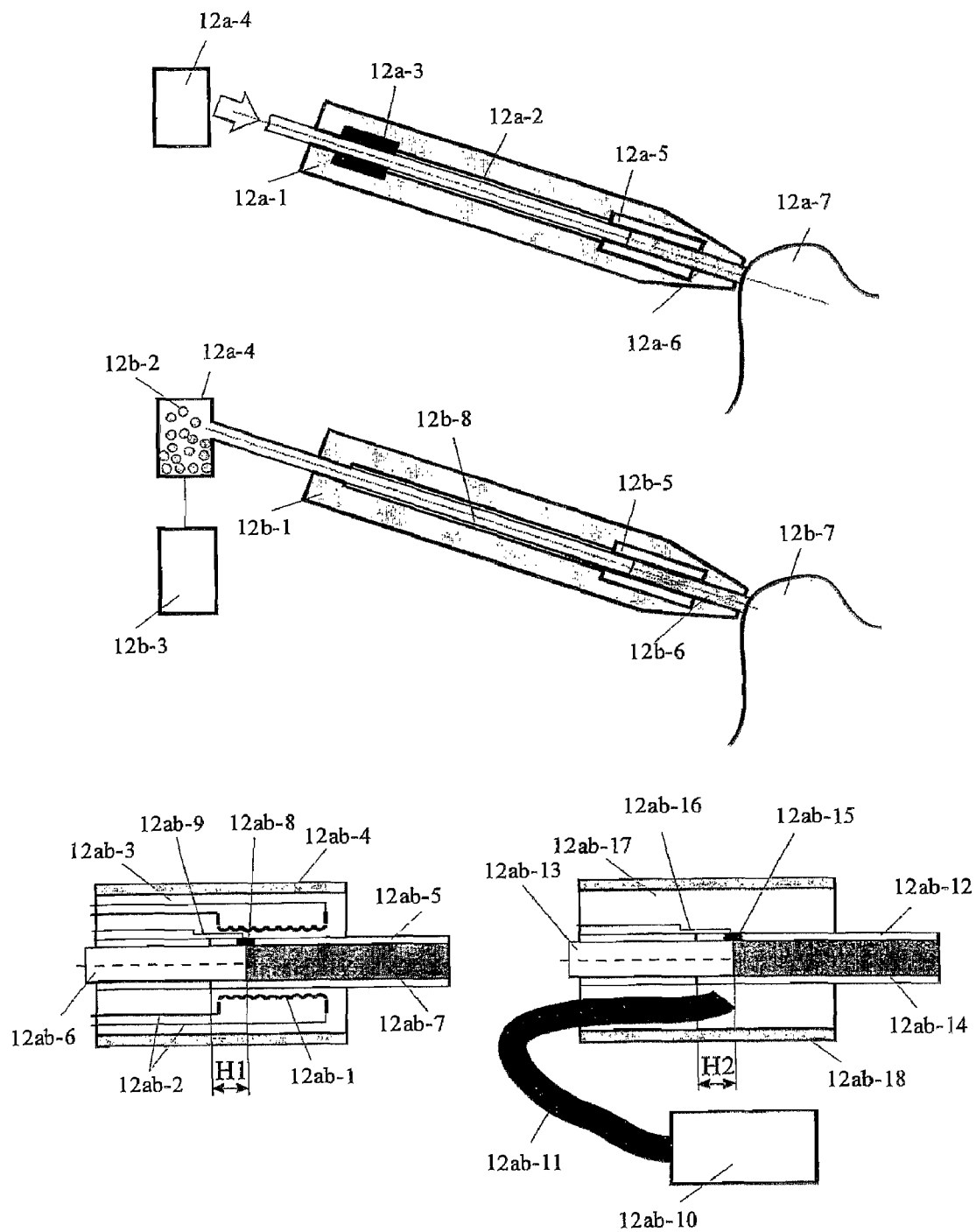
FIG. 12 is a schematic illustration of one of the embodiments of a device for treatment of hard tissue surface with melted solid-state material.

One embodiment is shown in FIG. 12. It comprises of a hand piece 12a-1, which contains a moving fiber 12a-2, made of sapphire, quarts, ceramic, fluoride glass, etc. The movement is accomplished by a mechanism 12a-3. The fiber is contained in a coil or container 12a-4. The device also contains a heater 12a-5, inside of which the fiber is melted. From the heater 12a-5, the melted material 12a-6 of fiber 12a-2 is delivered onto tooth enamel 12a-7 under pressure provided by the mechanism 12a-3. The heater 12a-5 can be one of the following: an electric heater, a non-coherent light source, a laser, a microwave source, an acoustic transformer, or a high-frequency electric current source, and a gas burner.

In yet another embodiment, shown in FIG. 12, the devices comprises of a hand piece 12b-1, which contains a tube 12b-8, along which solid-state particles 12b-2, such, sapphire, quartz, ceramic, fluoride glass, etc., move freely under pressure from the source 12b-5, which acts upon the particle container 12b-4. The device contains a heater 12b-5, inside of which melting of particles takes place. The melted material 12a-6 from the particles 12b-2 leaves the heater 12b-5 at a high speed and is delivered to the tooth enamel 12b-7. The heater 12a-5 can be one of the following: an electric heater, a laser, a microwave source, an acoustic transformer, or a high-frequency electric current source.

The heaters 12a-5 or 12b-5 can be electric heaters. An electric heater can be made from the wire fragment 12ab-1. An electric current is supplied to the wire fragment 12ab-1 via wires 12ab-2. The wire fragment 12ab-1 and partially wires 12ab-2 are placed in a thermo-insulated case 12ab-3 which is enclosed in another case 12ab-4 of the tip 12a-1 and 12b-1. The temperature of fragment 12ab-1, which is heated by current, is controlled by a change in its resistance. The heat generated by the fragment 12ab-1 via walls of tube 12ab-5 reaches the material of the fiber or particles 12ab-6. At a distance H1, from the entrance to the tube 12ab-5, the material of the wire and particles is melted, reaches tooth's surface 12a-7 (or 12b-7) via a tube 12ab-5 in a melted state 12ab-7. The temperature in the melting zone of the material 12ab-6 is controlled by a sensor 12ab-8, connected by wires 12ab-9 with the control unit of the device.

If the heater 12a-5 or 12b-5 is based on a laser, then the laser radiation source is 12ab-10. Laser radiation, conducted via an optical system 12ab-11, such as an optical fiber, reaches the tube 12ab-12 and is directed to the material of the wire or particles 12ab-13 via the walls of the tube. At a distance H2 from the entrance to the tube 12ab-12, the material of the wire and particles is melted and reaches the tooth surface 12a-7 (or 12b-7) in a melted state 12ab-14 via the tube 12ab-12. The temperature in the melting zone of the material 12ab-13 is controlled by a sensor 12ab-15, connected by wires 12ab-16 with the control unit of the device. The optical system and the tube are placed in a case 12ab-17, which, in turn, is situated in the case 12ab-18 of the tip 12a-1 (or 12b-1).

In the above embodiments, the distances between the heating zone and distal end of the contact tip is minimum in order not to cool down the melted fiber or particles, but sufficient to thermo-isolate the heater from the tooth. The method and apparatus described in this section is safer for tooth than direct heating because heating energy is applied to the filled material into the hand piece and not directly to the tissue. The rate of displacement of the melted compound is in the range of 0.1-1 mm³/s.

In practicing this method, after impregnating the SPS by liquified material, a modified, melted layer is formed, which may not be as even as the original enamel layer. The resulting unevenness may be corrected by a rotary, polishing instrument, which is outside of the scope of this invention.

The present method and apparatus for modification of hard tissue surface can also be used for repair or improvement of ceramic or composite fillings, crowns, veneers and implants.

All of the devices shown in FIGS. 10, 11, 12, 13, and 14 are provided with tooth safety features. The major safety risk with heating of a tooth is thermal damage to the pulpal tissues. Pulp damage occurs when the temperature of the pulp exceeds 45° C. for a short period of time and 42° C. for a longer period of time. To prevent overheating of the tooth pulp several methods and features are proposed in present invention:

1) The total amount of heating energy and average power, deposited on a treated tooth, is limited, and can be calculated using the formula:

$$P_{max} \cong \frac{4 - \Delta T - c - p - V - a}{\delta^2}, \tag{5}$$

where ΔT is temperature required to overheat the pulp (ΔT≈5° C., V is the tooth volume, and δ is the tooth thickness. Using the formula (4), the maximum average power of heat deposition on the tooth surface is approximately 0.3 W.

2) A cooling agent, such as gas or air-cooling, is applied to the tooth surface to remove part of the heating energy. The cooling agent can be directed at the treatment zone or to the area surrounding the treatment zone. When using cooling, the maximum power $P_{max}$ may be ten times greater than when not using cooling.

3) A temperature sensor could be used to monitor the temperature on the tooth surface and, based on this temperature, the heating energy and power can be controlled.

The method and apparatus for modification of dental hard tissue is not limited to dental hard tissue. The method and apparatus can also be used for treatment of other hard tissue in the human body and body of any mammal and animal. For example, the method of increasing chemical and wear resistance can be used in orthopedic surgery to improve such properties of a joint. In another embodiment, the method and apparatus can be used to improve wear resistance and aesthetic appearance of nail tissue. In practicing this method, a porous layer is first created on nail tissue using the above-described process of controlled etching by an acid based compound. The porous layer is then impregnated by solid-state nano and micro particles and heated to form a ceramic layer as previously described. The resulting ceramic layer has better mechanical and aesthetic properties than the original nail surface.

Recording Pictorial and Digital Information on Hard Tissue

The method of hard tissue surface modification can also be used for recording non-uniform distribution on optical properties of tooth surface, including, but limited to spatially modulated coefficient of scattering, refractive index, coefficient of absorption or fluorescence property. One of many purposes of such modulation is to create a picture for esthetic proposes, including, but limited to a tooth tattoo, or to record and store information, including, but not limited to text, numbers, an informational picture or a hologram. The novelty of this method is with tooth enamel being just one example of hard tissue of the human body where information can be recorded and stored for a long period of time. As one embodiment, the information can be recorded on a solid-state material surface with very high density. The information can be used for biometric identification of an individual, covert or overt, for security proposes or for identification of accident victims. For example, the information may include an individual's blood type, allergies and other types of data. The information can be recorded on the lingual surface of a tooth and can easily be read with standard optical methods, such as CCD camera or magnifying optics. In this case, the most effective method of recording is modulation of coefficient of absorption. Carbon nano particles can be used for this purpose. For esthetic reasons, identification information on the labial surface of anterior teeth can be recorded using modulation of refractive index, such as spatial grating, or using fluorescence substance or absorption substance in ultraviolet or infrared wavelength range. In one embodiment, etching of the hard tissue surface can be done through a mask, such as polymer film, with an opening, such as text or a picture. As a result, the text or the picture will form as a porous layer on the hard tissue surface. After this step, absorption or fluorescence nano particles are injected into the porous layer and solidified using polymer coating or via selective heating using one of the methods and apparatuses described above. In another embodiment, laser beam with computer-controlled scanner can be used for recording text or a picture.

Treatment and Repair of Dental Restorative Material

The proposed methods and apparatus for modification of the hard tissue surface can be used to modify and/or repair dental restorative materials, including, but not limited to (a) sealing of crown margins, (b) repairing fractured porcelain intra-orally, and (c) finishing porcelain post adjustment of crowns and filling material (a) Crowns and inlays, constructed of metals, ceramic resin materials, frequently fail as a result of a break down in the cement which fixes the restoration to the underlying tooth. The proposed method and apparatus can be used to provide a seal to the margin, thereby decreasing post insertion sensitivity due to marginal leakage, marginal breakdown and resulting recurrent caries. In one embodiment, solid-state nano and micro particles are impregnated into the margin, with a fluidity temperature lower or close to the temperature of melting of the restorative material and of the enamel. During selective heating, the melted particles fill the margin, forming a ceramic layer with mechanical, chemical and esthetic properties closely matching those of the restoration. In another embodiment compound preheated in handpiece (FIG. 12) is impregnating into the margin liquid state and after cooling filled margin and prevent leakage.

(b) All cemented porcelain crowns, bridges and inlays cannot be adequately repaired intraorally once the porcelain fractures. Current repair systems rely on air abrasion and/or acid etching of the fractured porcelain and then curing composite resin onto the damaged porcelain to replace the porcelain fractured. Such repairs are not very effective. Alternative methods require the whole restoration to be removed and redone—an expensive and time-consuming process. The proposed methods and apparatus can be used to repair fractures of restorative material intraorally, by impregnation of solid-state nano and micro particles into the fractures, with a fluidity temperature lower than the temperature of melting of the restorative material. During selective heating, the melted particles fill the pores of the restorative material and fuse with it, forming a ceramic layer with mechanical, chemical and esthetic properties closely matching those of the restoration.

(c) The overwhelming majority of laboratory formed ceramic restorations require occlusal adjustments, usually with diamond-coated burs, to correct the occlusion upon insertion of the restoration. This leaves a roughened porcelain surface, which leads to excessive wear of opposing teeth, hastens porcelain fracture and can be uncomfortable to the patient's tongue, lips and cheeks. Ideally, such a surface is reglazed it in a furnace. However, most dentists do not have such furnaces in their practices and are unfamiliar with their use. This necessitates returning the restoration to the laboratory for reglazing, needing another insertion appointment and perhaps another injection for insertion. The proposed method and apparatus can be used for intraoral reglazing of ceramic restorations or other finishing of ceramic surface. The reglazing can be conducted by selective heating and melting of surface of ceramic. In another embodiment over coating on ceramic can be applied using methods and apparatus described above.

Other Embodiments

While the invention has been described in conjunction with the detailed description thereof, the foregoing description is intended to illustrate and not to limit the scope of the invention, which is defined by the scope of the appended claims. Other aspects, advantages, and modifications are within the scope of the following claims. The use of "such as" and "for example" are only for the purposes of illustration and do not limit the nature or items within the classification.

What is claimed is:

1. A method of dental hard tissue modification comprising forming a superficial porous layer of the dental hard tissue and then selectively heating the superficial porous layer of the dental hard tissue to cause the superficial porous layer to fuse.

2. The method of claim 1, wherein selectively heating comprises acting on the superficial porous layer with a pulsed laser.

3. The method of claim 1, wherein a thickness of the superficial porous layer is between 0.5 µm and 100 µm.

4. The method of claim 1, wherein selectively heating comprises heating the superficial porous layer to a temperature higher than a melting temperature of the dental hard tissue but less than 2000° C.

5. The method of claim 1, further comprising forming the superficial porous layer of the dental hard tissue by using an acid before selectively heating the superficial porous layer.

6. The method of claim 1, further comprising cooling the superficial porous layer with a cooling fluid.

7. A method of dental hard tissue modification comprising:
   impregnating a superficial porous layer of the dental hard tissue with particles having a fluidity temperature about the same as a melting temperature of the dental hard tissue of the superficial porous layer; and
   selectively heating the superficial porous layer to a temperature higher than the melting temperature of the dental hard tissue, causing the dental hard tissue and the particles to fuse.

8. The method of claim 7, wherein the particles are inorganic particles.

9. The method of claim 8, wherein the inorganic particles are crystal, ceramic, glass or their mixture.

10. The method of claim 8, wherein the inorganic particles are name of $Na_2O$—$Al_2O_3$—$SiO_2$, $Ca(PO_3)$, $CaF_2$, $Ca_{10}(PO_4)_6(OH)_2$, and $Ca_{10}(PO_4)_6F_2$.

11. The method of claim 7, wherein selectively heating the superficial porous layer comprises heating by acoustic energy, electromagnetic energy, comprising light, microwave, radio frequency, and electric current, and combinations thereof.

12. A method of dental hard tissue modification comprising:
    impregnating a superficial porous layer of the dental hard tissue with particles having a fluidity temperature higher than a melting temperature of a hard tissue of the superficial porous layer; and
    selectively heating the superficial porous layer to a temperature higher than the melting temperature of the dental hard tissues, but lower than the fluidity temperature of the particles.

13. The method of claim 12, wherein selectively heating the superficial porous layer comprises heating by acoustic energy, electromagnetic energy, comprising light, microwave, radio frequency, and electric current, and combinations thereof.

14. The method of claim 12, wherein the particles are inorganic particles.

15. The method of claim 14, wherein the inorganic particles are made of crystal, ceramic, glass or their mixture.

16. The method of claim 15, wherein the particles are made of quartz glass or sitall glass.

17. The method of claim 15, wherein the particles are crystals selected from the group consisting of crystals of quartz, diamond, sapphire, topaz, amethyst, zircon, agate, granite, spinel, fianite, tanzanite, tourmaline and combinations thereof.

18. The method as in claim 1, 7 or 12, wherein the superficial porous layer is a carious lesion, open dentine, cementum, bone, or cartilage.

19. The method as in claim 1, 7 or 12, wherein the superficial porous layer is formed by applying the compound comprised of an acid.

20. The method as in claim 1, 7 or 12, wherein selectively heating the superficial porous layer is followed by active control cooling.

21. The method according to claim 20, wherein active control cooling is provided by water.

22. A method of dental hard tissue modification comprising:
    filling a superficial porous layer of the dental hard tissue with a fluidified material preheated above at least its fluidity temperature, wherein the fluidified material is glass, crystal or ceramic and mixture thereof; and
    letting the fluidified material cool and solidify in the superficial porous layer.

23. A method of dental hard tissue modification comprising:
    impregnating a porous surface of the dental hard tissue with particles having a fluidity temperature higher than a melting temperature of the dental hard tissue of the porous surface; and
    filling the porous surface with a material preheated above its fluidity temperature, wherein the material is glass, crystal or ceramic or mixture thereof, and wherein the fluidity temperature of the material is lower than a melting temperature of the particles and that of the dental hard tissue.

24. A method of dental hard tissue modification comprising forming a post-treatment layer having a composition differing from that of the dental hard tissue by selectively heating a superficial porous layer on the dental hard tissue.

25. The method of claim 24, comprising a step of forming the porous layer by applying to the dental hard tissue a composition having an acid before selectively heating the superficial porous layer.

26. The method of claim 24, comprising a step of impregnating the superficial porous layer with particles before selectively heating the superficial porous layer.

* * * * *